US010040829B2

(12) United States Patent
Mallet et al.

(10) Patent No.: US 10,040,829 B2
(45) Date of Patent: Aug. 7, 2018

(54) METHODS FOR PRODUCING PEPTIDES INCLUDING HERV-W ENVELOPE MOTIFS AND FOR PRODUCING ANTIBODIES SPECIFIC FOR THE PEPTIDES

(71) Applicant: BIOMERIEUX, Marcy-L'Etoile (FR)

(72) Inventors: Francois Mallet, Villeurbanne (FR); Guy Oriol, Saint Chamond (FR); Valerie Cheynet, Verin (FR)

(73) Assignee: BIOMERIEUX, Marcy-l'Etoile (FR)

( * ) Notice: Subject to any disclaimer, the term of this patent is extended or adjusted under 35 U.S.C. 154(b) by 0 days.

(21) Appl. No.: 14/847,941

(22) Filed: Sep. 8, 2015

(65) Prior Publication Data

US 2016/0090402 A1 Mar. 31, 2016

Related U.S. Application Data

(63) Continuation of application No. 12/087,893, filed as application No. PCT/FR2007/000236 on Feb. 9, 2007, now abandoned.

(30) Foreign Application Priority Data

Feb. 9, 2006 (FR) ..................... 06 50468

(51) Int. Cl.
| | | |
|---|---|---|
| C07K 14/005 | (2006.01) | |
| A61K 38/16 | (2006.01) | |
| A61K 39/12 | (2006.01) | |
| A61K 39/21 | (2006.01) | |
| C07K 16/10 | (2006.01) | |
| C12N 7/00 | (2006.01) | |

(52) U.S. Cl.
CPC .......... *C07K 14/005* (2013.01); *A61K 38/162* (2013.01); *A61K 39/12* (2013.01); *A61K 39/21* (2013.01); *C07K 16/1036* (2013.01); *C12N 7/00* (2013.01); *C07K 2317/34* (2013.01); *C12N 2740/10022* (2013.01); *C12N 2740/10034* (2013.01); *C12N 2740/10063* (2013.01); *G01N 2333/15* (2013.01)

(58) Field of Classification Search
None
See application file for complete search history.

(56) References Cited

U.S. PATENT DOCUMENTS

| 5,695,936 A | 12/1997 | Mandrand et al. |
| 2002/0155496 A1 | 10/2002 | Charles et al. |
| 2008/0038279 A1 | 2/2008 | Marche et al. |

FOREIGN PATENT DOCUMENTS

| FR | 2781802 A1 | 2/2000 |
| WO | 95/08000 A2 | 3/1995 |
| WO | 2005/080437 A1 | 9/2005 |

OTHER PUBLICATIONS

Nelson et al.,"Demystified". J. Clin. Pathol: Mol. Pathol. 53.,111-117, 2000.
Malassine et al.,"Expression of HERV-W Env Glycoprotein (syncytin) in the Extravillous Trophoblast of First Trimester Human Placenta." Placenta, 26(7):556-562, Aug. 2005.
Mi et al., "Syncytin is a Captive Retroviral Envelope Protein Involved in Human Placental Morphogenesis." Nature, 403, 785-789, Feb. 2000.
Mattson et al., "Ancient Viral Protein Enrages Astrocytes in Multiple Sclerosis." Nature Neuroscience, 7(10), 1021-1023. 2004.
Burkly et al.,"Synergistic Inhibition of Human Immunodeficiency Virus Type 1 Envelope Glycoprotein-Mediated Cell Fusion and Infection by an Antibody to CD4 Domain 2 in Combination." Journal of Virology, 69(7), 4267-4273.1995.
Crowell et al.,"Monoclonal Antibody That Inhibits Infection of He La and Rhabdomyosarcoma Cells by Selected Enteroviruses through Receptor Blockade." Journal of Virology, 57(2):438-445,1986.
Ochsenbauer-Jambor et al., "Novel Monoclonal Antibody Directed at the Receptor Binding Site on the Avian Sarcoma and Leukosis Virus Env Complex."Journal of Virology, 76(15)., 7518-7527, 2002.
Cheynet et al., "Synthesis, Assembly, and Processing of the Env ERVWEI/Syncytin Human Endogenous Retroviral Envelope", Journal of Virology, vol. 79, No. 9, pp. 5585-5593, May 2005.
La Villette et al., "The Envelope Glycoprotein of Human Endogenous Retrovirus Type W Uses a Divergent Family of Amino Acid Transporters/Cell Surface Receptors", Journal of Virology, vol. 76, No. 13, pp. 6442-6452, Jul. 2002.
Chang et al., "Functional Characterization of the Placental Fusogenic Membrane Protein Syncytin", Biology of Reproduction, vol. 71, pp. 1956-1962, Jul. 21, 2004.
Kim et al., "HTLV-I and -2 Envelope SU Subdomains and Critical Determinants in Receptor Binding", Retrovirology, vol. I, No. 41, pp. 1-14, Dec. 2, 2004.
Cheynet et al., "Identification of the hASCT2-binding domain of the Env ERVWEIISyncytin-1 Fusogenic Glycoprotein"; Retrovirology, vol. 3, No. 41, pp. 1-7, Jul. 4, 2006.
Altschul et al., "Basic Local Alignment Search Tool", J. Mo. Biol., vol. 215, pp. 403-410,1990.
Espinosa et al., "T-Ag Inhibits Implantation by EC Cell Derived Embryoid Bodies", Virus Genes, vol. 20, No. 3, pp. 195-200, 2000.
Tailor et al., "A Sodium-Dependent Neutral-Amino-Acid Transporter Mediates Infections of Feline and Baboon Endogenous Retroviruses and Simian Type D Retroviruses", Journal of Virology, vol. 73, No. 5, pp. 4470-4474, May 1999.

(Continued)

*Primary Examiner* — Nicole Kinsey White
(74) *Attorney, Agent, or Firm* — Oliff PLC

(57) ABSTRACT

A peptide domain necessary for an interaction between an envelope of a virus belonging to an HERV-W interference group and an hASCT receptor comprises (i) an N-terminus motif having an amino acid sequence selected from the group consisting of: SEQ ID No. 1 to SEQ ID No. 29, (ii) a C-terminus motif having an amino acid sequence selected from the group consisting of: SEQ ID No. 30 to SEQ ID No. 40, and (iii) at least one motif between the N-terminus and the C-terminus, and having an amino acid sequence selected from the group consisting of: SEQ ID No. 41, SEQ ID No. 42 and SEQ ID No. 73.

17 Claims, 13 Drawing Sheets

(56) References Cited

OTHER PUBLICATIONS

Rasko et al., "The RDI14/Simian Type D Retrovirus Receptor is a Neutral Amino Acid Transporter", Proc. Natl. Acad. Sci., USA, vol. 96, pp. 2129-2134, Mar. 1990.
Frendo et al., "Direct Involvement of HERV-W Env Glycoprotein in Human Trophoblast Cell Fusion and Differentiation", Molecular and Cellular Biology, vol. 23, No. 10, pp. 3566-3574, May 2003.
Walter, "Signal Sequence Recognition and Protein Targeting to the Endoplasmic Reticulum Membrane", Annu. Rev. Cell Biol., vol. 10, pp. 87-119, 1994.
Gossen et al., "Tight Control of Gene Expression in Mammalian Cells by tetracycline-Responsive Promoters", Proc. Natl. Acad. Sci., USA, vol. 89, pp. 5547-5551, Jun. 1992.
Huston et al., "Protein Engineering of Antibody Binding Sites: Recovery of Specific Activity in an Anti-Digoxin Single-Chain Fv Analogue Produced in *Escherichia coli*", Proc. Natl. Acad. Sci, USA, vol. 85, pp. 5879-5883, Aug. 1988.
Chevalier et al., "Biotin and Digoxigenin as Labels for Light and Electron Microscopy in Situ Hybridization Probes: Where Do We Stand?", The Journal of Histochemistry & Cytochemistry, vol. 45, No. 4, pp. 481-491, 1997.
Nisonoff et al., "Properties of the Major Component of a Peptic Digest of Rabbit Antibody", Science, vol. 132, pp. 1770-1771, Dec. 9, 1960.
Voisset et al., AIDS Research and Human Retroviruses, 2000, 16(8):731-740.

Env 197

Env 168

Env 169-317

Env 117

ENV 144

APPPCRCMTSSSPYQEFLWRMQRPGNIDAPSYRSLSKGTPTFTAHTHMPRNCYHSATLCMHANTHYW
TGKMINPSCPGGLGVTVCWTYFT<u>QTGMSDGGGYQDQAREKHV</u>KEVISQLTRVHGTSS

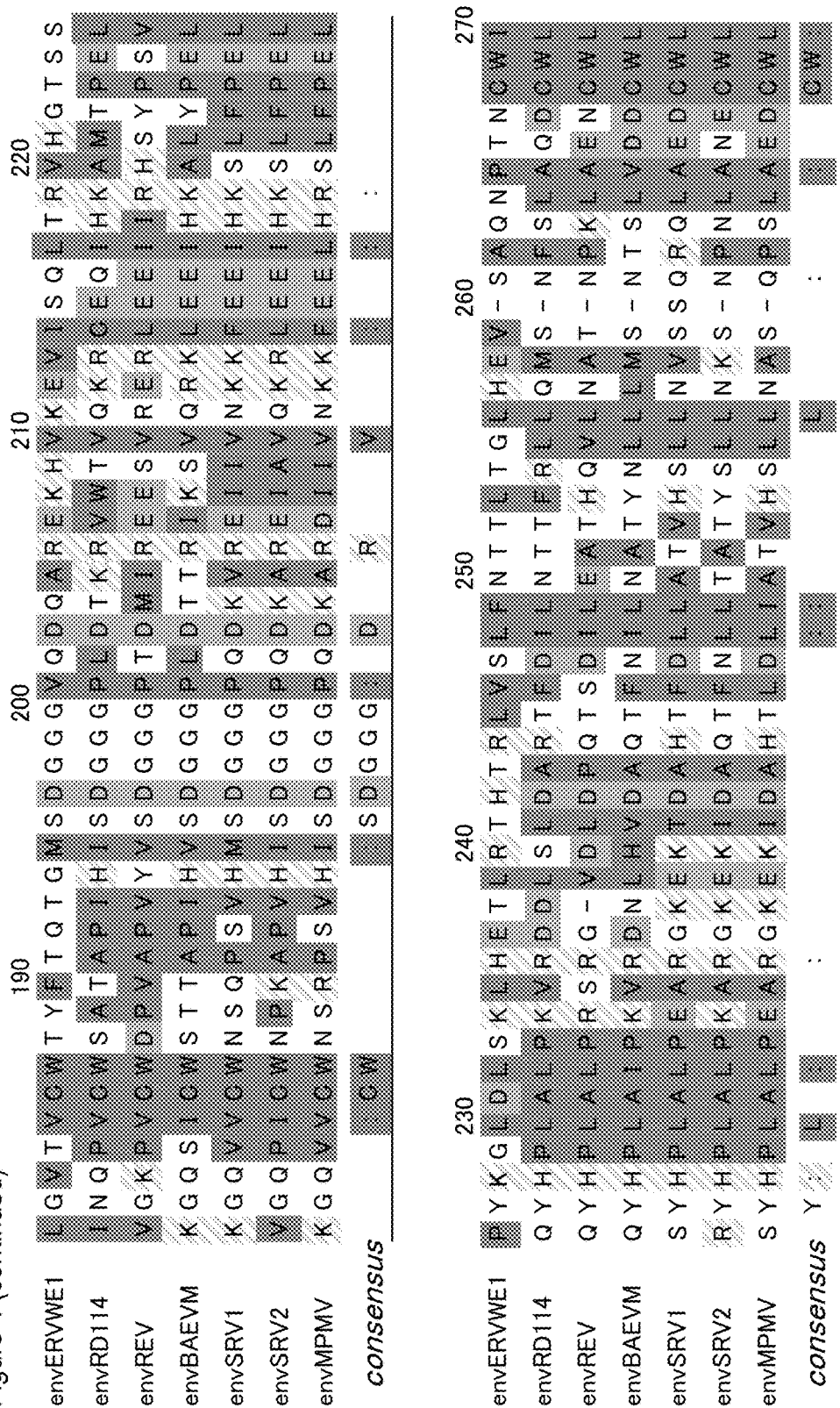

Figure 4 (continued)

| | | 460 | | 470 | | 480 | | 490 | |
|---|---|---|---|---|---|---|---|---|---|
| envERVWE1 | S T Q F Y Y K L S | Q E L N G | D M E R V A D | S L V T | L Q D Q L N | S L A A V V L | Q N R R A L D |
| envRD114  | S V T Q Y T K L S | H Q L I S | D V Q V L S G | T I Q | D L Q D Q V D | S L A E V V L | Q N R R G L D |
| envREV    | S V H T Y H K L S | N Q L I E | D V Q A L S T | I N D | L Q D Q V D | S L A E V V L | Q N R R G L D |
| envBAEVM  | S V T Q Y T K L S | N Q L I S | D V Q I L S S | T I Q | D L Q D Q V D | S L A E V V L | Q N R R G L D |
| envSRV1   | S L T Q Y T K L S | H Q L I S | D V Q A I S S | T I Q | D L Q D Q V D | S L A E V V L | Q N R R G L D |
| envSRV2   | S I T Q Y T K L S | R Q L I S | D V Q A I S S | T I Q | D L Q D Q V D | S L A E V V L | Q N R R G L D |
| envMPMV   | S I T Q Y T K L S | H Q L I S | D V Q A I S S | T I Q | D L Q D Q V D | S L A E V V L | Q N R R G L D |
| consensus | S           Y K L S | L | D | | L Q D Q | S L A | V V L | Q N R R   L D |

| | | 500 | | 510 | | 520 | | 530 | | 540 |
|---|---|---|---|---|---|---|---|---|---|---|
| envERVWE1 | L T A E R G G T | C L F L G | E E C C F Y Y V N Q S G | I V T E K V K E | I R D R L Q R R A E E L |
| envRD114  | L T A E Q G G I | C L A L Q | E K C C F Y A N K S G | I V R N K I R T | L Q E E L Q K R R E S L |
| envREV    | L T A E Q G G I | C L A L Q | E K C C F Y A D K S G | I V R D K I R K | L Q E D L E R R K D L |
| envBAEVM  | L T A E Q G G I | C L A L Q | E K C C F Y V N K S G | I V R D K I K T | L Q E E L E R R K D L |
| envSRV1   | L T A E Q G G I | C L A L Q | E K C C F Y A N K S G | I V R D K I K N | L Q D D L E K R R K Q L |
| envSRV2   | L T A E Q G G I | C L A L Q | E K C C F Y A N K S G | I V R D K I K R | L Q E D L E K R R K E L |
| envMPMV   | L T A E Q G G I | C L A L Q | E K C C F Y A N K S G | I V R D K I K N | L Q D D L E R R R Q L |
| consensus | L T A E   G G | C L   L | E   C C F Y   N   S G | I V   K | | R |

Figure 4 (continued)

|  | | 550 | | 560 | | 570 | | 580 | |
|---|---|---|---|---|---|---|---|---|---|
| envERVWE1 | R N T G P W G | L S S Q | W M P W I L P F F G | P F A A H L I I E G | P I I F N L L V N F V S |
| envRD114 | A T N P L W T | G L Q G | F G P Y I L P L L G | P L L T I L L T I T | I G P C V F S R L M A F I N |
| envREV | Y D N P L W S | G L N G | F G P C P Y I L P F L G | P L L T I F L T T | I G P Q I M K T L T R L I H |
| envBAEVM | A S N P L W T | G L Q G | L G P Y L L P F L G | P L L T I L L I T | I G P C I F N R L T A F I N |
| envSRV1 | I D N P L W T | G F H G | L C P Y V M P L L G | P L L C L T I V I | S F G P L I F N K L M T F L K |
| envSRV2 | I D N P L W T | G L H G | L C P Y L L P L L G | P L F C L L I T | F G P I I F N K J I T F V K |
| envMPMV | I D N P L W T | S F H G | F C P Y V M P L L G | P L L C L L I V I S | F G P L I F N K L N T F L K |
| consensus | . . N P L W . | . . . G | . . P . . . P . L G | P L . . . . . . | . G P . . F N . L . . F . . |

|  | | 590 | | 600 | | 610 | | 620 | | 630 |
|---|---|---|---|---|---|---|---|---|---|---|
| envERVWE1 | S R I E A V K | - - - L Q | M E R K M Q S K T K I Y | R R P L D R P A S P R | S D V N D I K G T |
| envRD114 | D R I N V H A | M V L A Q | Q Y Q A L K A E E E A Q D | - - - - - - - - - | - - - - - - - - |
| envREV | D K K Q A V K | I T A L V | P Q Y K P L P T E M D T L G Q | - - - - - - - - - | - - - - - - - - |
| envBAEVM | D K K N I I H A | M V I T Q | Q Y Q V E R T E E E A Q D | - - - - - - - - - | - - - - - - - - |
| envSRV1 | H Q I E S I Q | A K P I Q | V H Y H R L E E D H G G S Y L N L T | - - - - - - - | - - - - - - - - |
| envSRV2 | Q Q I D A I Q | A K P I Q | V H Y H R L E E D N G G W Y L R V S | - - - - - - - | - - - - - - - - |
| envMPMV | H Q I E S I Q | A K P I Q | V H Y H R L E E Q E D S G G S Y L T L T | - - - - - - | - - - - - - - - |
| consensus | . . I . . . . | . . . . . | . . . . . . . . . . . . . . . | | |

SEQUENCE LISTING

```
<160> NUMBER OF SEQ ID NOS: 85

<210> SEQ ID NO 1
<211> LENGTH: 6
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid
```

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1

Xaa Xaa Pro Cys Xaa Cys
1               5

<210> SEQ ID NO 2
<211> LENGTH: 7
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Xaa Xaa Xaa Pro Cys Xaa Cys
1               5

<210> SEQ ID NO 3
<211> LENGTH: 8
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Xaa Xaa Xaa Xaa Pro Cys Xaa Cys
1               5

<210> SEQ ID NO 4
<211> LENGTH: 9
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 4

Xaa Xaa Xaa Xaa Xaa Pro Cys Xaa Cys
1               5

<210> SEQ ID NO 5
<211> LENGTH: 10
<212> TYPE: PRT
<213> ORGANISM: Artificial
```

```
<220> FEATURE:
<223> OTHER INFORMATION: synthetic construct
<220> FEATURE:
<221> NAME/KEY: misc_feature
<222> LOCATION: (1)

-continued

```
<210> SEQ ID NO 9
<211> LENGTH: 14
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 9

Xaa Xaa Xaa Xaa Xaa Xaa Xaa Xaa Xaa Xaa Pro Cys Xaa Cys
1               5                   10

<210> SEQ ID NO 10
<211> LENGTH: 15
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 10

Xaa Xaa Xaa Xaa Xaa Xaa Xaa Xaa Xaa Xaa Xaa Pro Cys Xaa Cys
1               5                   10                  15

<210> SEQ ID NO 11
<211> LENGTH: 16
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 11

Xaa Xaa Xaa Xaa Xaa Xaa Xaa Xaa Xaa Xaa Xaa Xaa Pro Cys Xaa Cys
1               5                   10                  15

<210> SEQ ID NO 12
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
```

```
<400> SEQUENCE: 12

Xaa Xaa Xaa Xaa Xaa Xaa Xaa Xaa Xaa Xaa Xaa Xaa Xaa Pro Cys Xaa
1               5                   10                  15

Cys

<210> SEQ ID NO 13
<211> LENGTH: 18
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 13

Xaa Xaa Xaa Xaa Xaa Xaa Xaa Xaa Xaa Xaa Xaa Xaa Xaa Xaa Pro Cys
1               5                   10                  15

Xaa Cys

<210> SEQ ID NO 14
<211> LENGTH: 19
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 14

Xaa Xaa Xaa Xaa Xaa Xaa Xaa Xaa Xaa Xaa Xaa Xaa Xaa Xaa Xaa Pro
1               5                   10                  15

Cys Xaa Cys

<210> SEQ ID NO 15
<211> LENGTH: 20
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Pro Cys Xaa Cys
            20
```

```
<210> SEQ ID NO 16
<211> LENGTH: 21
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Pro Cys Xaa Cys
        20

<210> SEQ ID NO 17
<211> LENGTH: 22
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Pro Cys Xaa Cys
        20

<210> SEQ ID NO 18
<211> LENGTH: 23
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

Xaa Xaa Xaa Pro Cys Xaa Cys
        20

<210> SEQ ID NO 19
<211> LENGTH: 24
<212> TYPE: PRT
<213> ORGANISM: Artificial
<220> FEATURE:
<223> OTHER INFORMATION: synthetic construct
```

```
<220> FEATURE:
<221> NAME/KEY: misc_feature
<222> LOCATION: (1)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Cys Xaa Cys
            20

<210> SEQ ID NO 20
<211> LENGTH: 25
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 20

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Pro Cys Xaa Cys
            20                  25

<210> SEQ ID NO 21
<211> LENGTH: 26
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 21

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Cys Xaa Cys
            20                  25

<210> SEQ ID NO 22
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)
<223> OTHER INFORMATION: Xaa can be any naturally occurring amino acid
```

```
<220> FEATURE:
<221> NAME/KEY: misc_feature
<222> LOCATION: (26)..(26)
<223> OTHER INFORMATION: Xaa can be any naturally occurring amino acid

<400> SEQUENCE: 22

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Cys Xaa Cys
            20                  25

<210> SEQ ID NO 23
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 23

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Cys Xaa Cys
            20                  25

<210> SEQ ID NO 24
<211> LENGTH: 29
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 24

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Cys Xaa Cys
            20                  25

<210> SEQ ID NO 25
<211> LENGTH: 30
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
```

<400> SEQUENCE: 25

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Pro Cys Xaa Cys
            20                  25                  30

<210> SEQ ID NO 26
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 26

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Pro Cys Xaa Cys
            20                  25                  30

<210> SEQ ID NO 27
<211> LENGTH: 32
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Pro Cys Xaa Cys
            20                  25                  30

<210> SEQ ID NO 28
<211> LENGTH: 33
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Pro Cys Xaa
            20                  25                  30

Cys

<210> SEQ ID NO 29
<211> LENGTH: 34
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 29

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Pro Cys
            20                  25                  30

Xaa Cys

<210> SEQ ID NO 30
<211> LENGTH: 25
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(25)
<223> OTHER INFORMATION: Xaa can be any naturally occurring amino acid

<400> SEQUENCE: 30

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa
            20                  25

```
<210> SEQ ID NO 31
<211> LENGTH: 26
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(26)
<223> OTHER INFORMATION: Xaa can be any naturally occurring amino acid

<400> SEQUENCE: 31

Ser Asp Xaa Xaa Xaa Xaa Xaa Asp Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 32
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(27)
<223> OTHER INFORMATION: Xaa can be any naturally occurring amino acid

<400> SEQUENCE: 32

Ser Asp Xaa Xaa Xaa Xaa Xaa Asp Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25
```

```
<210> SEQ ID NO 33
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(28)
<223> OTHER INFORMATION: Xaa can be any naturally occurring amino acid

<400> SEQUENCE: 33

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 34
<211> LENGTH: 29
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(29)
<223> OTHER INFORMATION: Xaa can be any naturally occurring amino acid

<400> SEQUENCE: 34

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25
```

```
<210> SEQ ID NO 35
<211> LENGTH: 30
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(30)
<223> OTHER INFORMATION: Xaa can be any naturally occurring amino acid

<400> SEQUENCE: 35

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

<210> SEQ ID NO 36
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(31)
<223> OTHER INFORMATION: Xaa can be any naturally occurring amino acid

<400> SEQUENCE: 36

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30
```

```
<210> SEQ ID NO 37
<211> LENGTH: 32
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(32)
<223> OTHER INFORMATION: Xaa can be any naturally occurring amino acid

<400> SEQUENCE: 37

Ser Asp Xaa Xaa Xaa Xaa Xaa Asp Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 38
<211> LENGTH: 33
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(33)
<223> OTHER INFORMATION: Xaa can be any naturally occurring amino acid
```

<400> SEQUENCE: 38

Ser Asp Xaa Xaa Xaa Xaa Xaa Asp Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 39
<211> LENGTH: 34
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(34)
<223> OTHER INFORMATION: Xaa can be any naturally occurring amino acid

<400> SEQUENCE: 39

Ser Asp Xaa Xaa Xaa Xaa Xaa Asp Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 40
<211> LENGTH: 35
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

```
<220> FEATURE:
<221> NAME/KEY: misc_feature
<222> LOCATION: (11)..(35)
<223> OTHER INFORMATION: Xaa can be any naturally occurring amino acid

<400> SEQUENCE: 40

Ser Asp Xaa Xaa Xaa Xaa Xaa Asp Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa
35

<210> SEQ ID NO 41
<211> LENGTH: 8
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 41

Cys Tyr Xaa Xaa Xaa Xaa Xaa Cys
1               5

<210> SEQ ID NO 42
<211> LENGTH: 12
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 42

Cys Xaa Xaa Xaa Xaa Xaa Xaa Xaa Xaa Cys Trp
1               5                   10

<210> SEQ ID NO 43
<211> LENGTH: 10
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 43

Ser Asp Xaa Xaa Xaa Xaa Xaa Asp Xaa Xaa
1               5                   10

<210> SEQ ID NO 44
<211> LENGTH: 6
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is aspartic acid, glutamic acid or arginine

<400> SEQUENCE: 44

Xaa Xaa Pro Cys Xaa Cys
1               5

<210> SEQ ID NO 45
<211> LENGTH: 7
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is aspartic acid, glutamic acid or arginine
```

```
<400> SEQUENCE: 45

Xaa Xaa Xaa Pro Cys Xaa Cys
1               5

<210> SEQ ID NO 46
<211> LENGTH: 8
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is aspartic acid, glutamic acid or arginine

<400> SEQUENCE: 46

Xaa Xaa Xaa Xaa Pro Cys Xaa Cys
1               5

<210> SEQ ID NO 47
<211> LENGTH: 9
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is aspartic acid, glutamic acid or arginine

<400> SEQUENCE: 47

Xaa Xaa Xaa Xaa Xaa Pro Cys Xaa Cys
1               5

<210> SEQ ID NO 48
<211> LENGTH: 10
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is aspartic acid, glutamic acid or arginine

<400> SEQUENCE: 48

Xaa Xaa Xaa Xaa Xaa Xaa Pro Cys Xaa Cys
1               5                   10

<210> SEQ ID NO 49
<211> LENGTH: 11
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(7)
<223> OTHER INFORMATION: Xaa can be any naturally occurring amino acid
```

```
<220> FEATURE:
<221> NAME/KEY: misc_feature
<222> LOCATION: (10)..(10)
<223> OTHER INFORMATION: Xaa is aspartic acid, glutamic acid or arginine

<400> SEQUENCE: 49

Xaa Xaa Xaa Xaa Xaa Xaa Xaa Pro Cys Xaa Cys
1               5                   10

<210> SEQ ID NO 50
<211> LENGTH: 12
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa is aspartic acid, glutamic acid or arginine

<400> SEQUENCE: 50

Xaa Xaa Xaa Xaa Xaa Xaa Xaa Xaa Pro Cys Xaa Cys
1               5                   10

<210> SEQ ID NO 51
<211> LENGTH: 13
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa is aspartic acid, glutamic acid or arginine

<400> SEQUENCE: 51

Xaa Xaa Xaa Xaa Xaa Xaa Xaa Xaa Xaa Pro Cys Xaa Cys
1               5                   10

<210> SEQ ID NO 52
<211> LENGTH: 14
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is aspartic acid, glutamic acid or arginine

<400> SEQUENCE: 52

Xaa Xaa Xaa Xaa Xaa Xaa Xaa Xaa Xaa Xaa Pro Cys Xaa Cys
1               5                   10

<210> SEQ ID NO 53
<211> LENGTH: 15
<212> TYPE: PRT
<213> ORGANISM: Artificial
```

<220> FEATURE:
<223> OTHER INFORMATION: synthetic construct
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is aspartic acid, glutamic acid or arginine

<400> SEQUENCE: 53

Xaa Xaa Xaa Xaa Xaa Xaa Xaa Xaa Xaa Xaa Xaa Pro Cys Xaa Cys
1               5                   10                  15

<210> SEQ ID NO 54
<211> LENGTH: 16
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa is aspartic acid, glutamic acid or arginine

<400> SEQUENCE: 54

Xaa Xaa Xaa Xaa Xaa Xaa Xaa Xaa Xaa Xaa Xaa Xaa Pro Cys Xaa Cys
1               5                   10                  15

<210> SEQ ID NO 55
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa is aspartic acid, glutamic acid or arginine

<400> SEQUENCE: 55

Xaa Xaa Xaa Xaa Xaa Xaa Xaa Xaa Xaa Xaa Xaa Xaa Xaa Pro Cys Xaa
1               5                   10                  15

Cys

<210> SEQ ID NO 56
<211> LENGTH: 18
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa is aspartic acid, glutamic acid or arginine

```
<400> SEQUENCE: 56

Xaa Xaa Xaa Xaa Xaa Xaa Xaa Xaa Xaa Xaa Xaa Xaa Xaa Xaa Pro Cys
1               5                   10                  15

Xaa Cys

<210> SEQ ID NO 57
<211> LENGTH: 19
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa is aspartic acid, glutamic acid or arginine

<400> SEQUENCE: 57

Xaa Xaa Xaa Xaa Xaa Xaa Xaa Xaa Xaa Xaa Xaa Xaa Xaa Xaa Xaa Pro
1               5                   10                  15

Cys Xaa Cys

<210> SEQ ID NO 58
<211> LENGTH: 20
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is aspartic acid, glutamic acid or arginine

<400> SEQUENCE: 58

Xaa Xaa Xaa Xaa Xaa Xaa Xaa Xaa Xaa Xaa Xaa Xaa Xaa Xaa Xaa Xaa
1               5                   10                  15

Pro Cys Xaa Cys
            20

<210> SEQ ID NO 59
<211> LENGTH: 21
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa is aspartic acid, glutamic acid or arginine

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Pro Cys Xaa Cys
            20
```

```
<210> SEQ ID NO 60
<211> LENGTH: 22
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa is aspartic acid, glutamic acid or arginine

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Xaa Xaa Pro Cys Xaa Cys
            20

<210> SEQ ID NO 61
<211> LENGTH: 23
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa is aspartic acid, glutamic acid or arginine

<400> SEQUENCE: 61

Xaa Xaa Xaa Xaa Xaa Xaa Xaa Xaa Xaa Xaa Xaa Xaa Xaa Xaa Xaa Xaa
1               5                   10                  15

Xaa Xaa Xaa Pro Cys Xaa Cys
            20

<210> SEQ ID NO 62
<211> LENGTH: 24
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa is aspartic acid, glutamic acid or arginine

<400> SEQUENCE: 62

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Cys Xaa Cys
            20

<210> SEQ ID NO 63
<211> LENGTH: 25
<212> TYPE: PRT
<213> ORGANISM: Artificial
<220> FEATURE:
<223> OTHER INFORMATION: synthetic construct
```

```
<220> FEATURE:
<221> NAME/KEY: misc_feature
<222> LOCATION: (1)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is aspartic acid, glutamic acid or arginine

<400> SEQUENCE: 63

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Pro Cys Xaa Cys
            20                  25

<210> SEQ ID NO 64
<211> LENGTH: 26
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa is aspartic acid, glutamic acid or arginine

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Cys Xaa Cys
            20                  25

<210> SEQ ID NO 65
<211> LENGTH: 27
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa is aspartic acid, glutamic acid or arginine

<400> SEQUENCE: 65

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Pro Cys Xaa Cys
            20                  25

<210> SEQ ID NO 66
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(24)
<223> OTHER INFORMATION: Xaa can be any naturally occurring amino acid
```

```
<220> FEATURE:
<221> NAME/KEY: misc_feature
<222> LOCATION: (27)..(27)
<223> OTHER INFORMATION: Xaa is aspartic acid, glutamic acid or arginine

<400> SEQUENCE: 66

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Cys Xaa Cys
            20                  25

<210> SEQ ID NO 67
<211> LENGTH: 29
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is aspartic acid, glutamic acid or arginine

<400> SEQUENCE: 67

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Pro Cys Xaa Cys
            20                  25

<210> SEQ ID NO 68
<211> LENGTH: 30
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa is aspartic acid, glutamic acid or arginine

<400> SEQUENCE: 68

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Pro Cys Xaa Cys
            20                  25                  30

<210> SEQ ID NO 69
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa is aspartic acid, glutamic acid or arginine
```

```
<400> SEQUENCE: 69

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Pro Cys Xaa Cys
            20                  25                  30

<210> SEQ ID NO 70
<211> LENGTH: 32
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa is aspartic acid, glutamic acid or arginine

<400> SEQUENCE: 70

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Pro Cys Xaa Cys
            20                  25                  30

<210> SEQ ID NO 71
<211> LENGTH: 33
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa is aspartic acid, glutamic acid or arginine

<400> SEQUENCE: 71

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Pro Cys Xaa
            20                  25                  30

Cys

<210> SEQ ID NO 72
<211> LENGTH: 34
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (1)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa is aspartic acid, glutamic acid or arginine
```

-continued

<400> SEQUENCE: 72

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Pro Cys
                20                  25                  30

Xaa Cys

<210> SEQ ID NO 73
<211> LENGTH: 11
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 73

Cys Xaa Xaa Xaa Xaa Xaa Xaa Xaa Xaa Cys Trp
1               5                   10

<210> SEQ ID NO 74
<211> LENGTH: 124
<212> TYPE: PRT
<213> ORGANISM: Artificial Sequence
<220> FEATURE:
<223> OTHER INFORMATION: snythetic construct

<400> SEQUENCE: 74

Ala Pro Pro Pro Cys Arg Cys Met Thr Ser Ser Pro Tyr Gln Glu
1               5                   10                  15

Phe Leu Trp Arg Met Gln Arg Pro Gly Asn Ile Asp Ala Pro Ser Tyr
                20                  25                  30

Arg Ser Leu Ser Lys Gly Thr Pro Thr Phe Thr Ala His Thr His Met
            35                  40                  45

Pro Arg Asn Cys Tyr His Ser Ala Thr Leu Cys Met His Ala Asn Thr
        50                  55                  60

His Tyr Trp Thr Gly Lys Met Ile Asn Pro Ser Cys Pro Gly Gly Leu
65                  70                  75                  80

Gly Val Thr Val Cys Trp Thr Tyr Phe Thr Gln Thr Gly Met Ser Asp
            85                  90                  95

Gly Gly Gly Val Gln Asp Gln Ala Arg Glu Lys His Val Lys Glu Val
        100                 105                 110

Ile Ser Gln Leu Thr Arg Val His Gly Thr Ser Ser
        115                 120

<210> SEQ ID NO 75
<211> LENGTH: 538
<212> TYPE: PRT
<213> ORGANISM: Homo sapiens

<400> SEQUENCE: 75

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

```
Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
                420                 425                 430

Arg Asn Thr Gly Pro Trp Gly Leu Leu Ser Gln Trp Met Pro Trp Ile
            435                 440                 445

Leu Pro Phe Leu Gly Pro Leu Ala Ala Ile Ile Leu Leu Leu Leu Phe
        450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
    530                 535

<210> SEQ ID NO 76
<211> LENGTH: 564
<212> TYPE: PRT
<213> ORGANISM: RD114 retrovirus

<400> SEQUENCE: 76

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Gly Pro Leu Asp Thr Lys Arg Val
                165                 170                 175
```

```
Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
        275                 280                 285

Ser Pro Phe Ile Asn Asp Thr Glu Gln Ile Asp Leu Gly Ala Val Thr
    290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
            340                 345                 350

Asp Ile Asp Ile Asn Pro Gly Asp Glu Pro Val Pro Ile Pro Ala Ile
        355                 360                 365

Asp His Tyr Ile His Arg Pro Lys Arg Ala Val Gln Phe Ile Pro Leu
    370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
            420                 425                 430

Val Asp Ser Leu Ala Glu Val Val Leu Gln Asn Arg Arg Gly Leu Asp
        435                 440                 445

Leu Leu Thr Ala Glu Gln Gly Gly Ile Cys Leu Ala Leu Gln Glu Lys
    450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Thr Asn
                485                 490                 495

Pro Leu Trp Thr Gly Leu Gln Gly Phe Leu Pro Tyr Leu Leu Pro Leu
            500                 505                 510

Leu Gly Pro Leu Leu Thr Leu Leu Ile Leu Thr Ile Gly Pro Cys
        515                 520                 525

Val Phe Ser Arg Leu Met Ala Phe Ile Asn Asp Arg Leu Asn Val Val
    530                 535                 540

His Ala Met Val Leu Ala Gln Gln Tyr Gln Ala Leu Lys Ala Glu Glu
545                 550                 555                 560

Glu Ala Gln Asp

<210> SEQ ID NO 77
<211> LENGTH: 567
<212> TYPE: PRT
<213> ORGANISM: Av

```
<400> SEQUENCE: 77

Met Asp Cys Leu Thr Asn Leu Arg Ser Ala Glu Gly Lys Val Asp Gln
1               5                   10                  15

Ala Ser Lys Ile Leu Ile Leu Val Ala Trp Trp Gly Phe Gly Thr
            20                  25                  30

Thr Ala Glu Gly Tyr Pro Leu Gln Gln Leu Trp Glu Leu Pro Cys Asp
        35                  40                  45

Cys Ser Gly Gly Tyr Val Ser Ser Ile Pro Thr Tyr Tyr Thr Tyr Ser
    50                  55                  60

Leu Asp Cys Gly Gly Ser Thr Ala Tyr Leu Thr Tyr Gly Ser Gly Thr
65                  70                  75                  80

Gly Ser Trp Ser Trp Gly Gly Phe Lys Gln Gln Trp Glu Cys Val
                85                  90                  95

Phe Lys Pro Lys Ile Ile Pro Ser Val Gln Gly Gln Pro Gly Pro Cys
            100                 105                 110

Pro Ser Glu Cys Leu Gln Ile Ala Thr Gln Met His Ser Thr Cys Tyr
        115                 120                 125

Glu Lys Thr Gln Glu Cys Thr Leu Leu Gly Lys Thr Tyr Phe Thr Ala
    130                 135                 140

Ile Leu Gln Lys Thr Lys Leu Gly Ser Tyr Glu Asp Gly Pro Asn Lys
145                 150                 155                 160

Leu Ile Gln Ala Ser Cys Thr Gly Thr Val Gly Lys Pro Val Cys Trp
                165                 170                 175

Asp Pro Val Ala Pro Val Tyr Val Ser Asp Gly Gly Pro Thr Asp
            180                 185                 190

Met Ile Arg Glu Glu Ser Val Arg Glu Arg Leu Glu Glu Ile Ile Arg
        195                 200                 205

His Ser Tyr Pro Ser Val Gln Tyr His Pro Leu Ala Leu Pro Arg Ser
    210                 215                 220

Arg Gly Val Asp Leu Asp Pro Gln Thr Ser Asp Ile Leu Glu Ala Thr
225                 230                 235                 240

His Gln Val Leu Asn Ala Thr Asn Pro Lys Leu Ala Glu Asn Cys Trp
                245                 250                 255

Leu Cys Met Thr Leu Gly Thr Pro Ile Pro Ala Ala Ile Pro Thr Asn
            260                 265                 270

Gly Asn Val Thr Leu Asp Gly Asn Cys Ser Leu Ser Leu Pro Phe Gly
        275                 280                 285

Cys Asn Pro Pro Gly Ser Ile Asp Val Ser Cys Tyr Ala Gly Glu Ala
    290                 295                 300

Asp Asn Arg Thr Gly Ile Pro Val Gly Tyr Val His Phe Thr Asn Cys
305                 310                 315                 320

Thr Ser Ile Gln Glu Val Thr Asn Glu Thr Ser Gln Met Gly Asn Leu
                325                 330                 335

Thr Arg Leu Cys Pro Pro Gly His Val Phe Val Cys Gly Asn Asn
            340                 345                 350

Met Ala Tyr Thr Ala Leu Pro Asn Lys Trp Ile Gly Leu Cys Ile Leu
        355                 360                 365

Ala Ser Ile Val Pro Asp Ile Ser Ile Ser Gly Glu Glu Pro Ile
    370                 375                 380

Pro Leu Pro Ser Ile Glu Tyr Thr Ala Arg Arg His Lys Arg Ala Val
385                 390                 395                 400

Gln Phe Ile Pro Leu Leu Val Gly Leu Gly Ile Ser Gly Ala Thr Leu
                405                 410                 415
```

```
Ala Gly Gly Thr Gly Leu Gly Val Ser Val His Thr Tyr His Lys Leu
            420                 425                 430

Ser Asn Gln Leu Ile Glu Asp Val Gln Ala Leu Ser Gly Thr Ile Asn
            435                 440                 445

Asp Leu Gln Asp Gln Ile Asp Ser Leu Ala Glu Val Val Leu Gln Asn
450                 455                 460

Arg Arg Gly Leu Asp Leu Leu Thr Ala Glu Gln Gly Gly Ile Cys Leu
465                 470                 475                 480

Ala Leu Gln Glu Lys Cys Cys Phe Tyr Ala Asn Lys Ser Gly Ile Val
            485                 490                 495

Arg Asp Lys Ile Arg Lys Leu Gln Glu Asp Leu Ile Glu Arg Lys Arg
            500                 505                 510

Ala Leu Tyr Asp Asn Pro Leu Trp Ser Gly Leu Asn Gly Phe Leu Pro
            515                 520                 525

Tyr Leu Leu Pro Leu Leu Gly Pro Leu Phe Gly Leu Ile Leu Phe Leu
            530                 535                 540

Thr Leu Gly Pro Cys Ile Met Lys Thr Leu Thr Arg Ile Ile His Asp
545                 550                 555                 560

Lys Ile Gln Ala Val Lys Ser
            565

<210> SEQ ID NO 78
<211> LENGTH: 563
<212> TYPE: PRT
<213> ORGANISM: Baboon endogenous virus

<400> SEQUENCE: 78

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
            85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
            115                 120                 125

Thr Ser Asp Val Gln Val Leu Gly Ser Thr Asn Lys Leu Ile Gln Ser
            130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Pro Leu Asp Thr Thr Arg Ile
            165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
            195                 200                 205

Met Val Asp Ala Gln Thr Leu Asn Ile Leu Asn Ala Thr Tyr Asn Leu
210                 215                 220
```

```
Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
            245                 250                 255

Tyr Val Thr Arg Ser Ser Asp Asn Ile Ser Cys Leu Ile Ile Pro Pro
                260                 265                 270

Leu Leu Val Gln Pro Met Gln Phe Ser Asn Ser Ser Cys Leu Phe Ser
            275                 280                 285

Pro Ser Tyr Asn Ser Thr Glu Glu Ile Asp Leu Gly His Val Ala Phe
        290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala Met Val Leu Thr Gln Gln Tyr Gln Val Leu Arg Thr Asp Glu Glu
545                 550                 555                 560

Ala Gln Asp

<210> SEQ ID NO 79
<211> LENGTH: 587
<212> TYPE: PRT
<213> ORGANISM: Simian retrovirus SRV-1

<400> SEQUENCE: 79

Met Asn Phe Asn His His Phe Thr Trp Ser Leu Val Ile Ile Ser Gln
1               5                   10                  15

Ile Phe Gln Val Gln Ala Gly Phe Gly Asp Pro Arg Glu Ala Leu Leu
            20                  25                  30
```

```
Glu Ile Gln Gln Lys His Gly Lys Pro Cys Asp Cys Ala Gly Gly Tyr
     35                  40                  45

Val Ser Ser Pro Pro Thr Asn Ser Leu Thr Thr Val Ser Cys Ser Thr
 50                  55                  60

Tyr Thr Ala Tyr Ser Val Thr Asn Ser Leu Lys Trp Gln Cys Val Ser
 65                  70                  75                  80

Thr Pro Thr Thr Ala Ser Pro Thr His Ile Gly Ser Cys Pro Ser Gln
                 85                  90                  95

Cys Asn Ser Gln Ser Tyr Asp Ser Val His Ala Thr Cys Tyr Asn His
             100                 105                 110

Tyr Gln Gln Cys Thr Ile Gly Asn Lys Thr Tyr Leu Thr Ala Thr Met
         115                 120                 125

Ile Arg Asp Lys Ser Pro Ser Ser Gly Asp Gly Asn Val Pro Thr Ile
 130                 135                 140

Leu Gly Asn Asn Gln Asn Leu Ile Ile Ala Gly Cys Pro Glu Asn Lys
 145                 150                 155                 160

Lys Gly Gln Val Val Cys Trp Asn Ser Gln Pro Ser Val His Met Ser
                 165                 170                 175

Asp Gly Gly Gly Pro Gln Asp Lys Val Arg Glu Ile Ile Val Asn Lys
             180                 185                 190

Lys Phe Glu Glu Leu His Lys Ser Leu Phe Pro Glu Leu Ser Tyr His
         195                 200                 205

Pro Leu Ala Leu Pro Glu Ala Arg Gly Lys Glu Lys Ile Asp Ala His
 210                 215                 220

Thr Phe Asp Leu Leu Ala Thr Val His Ser Leu Leu Asn Val Ser Ser
 225                 230                 235                 240

Gln Arg Gln Leu Ala Glu Asp Cys Trp Leu Cys Leu Arg Ser Gly Asp
                 245                 250                 255

Pro Val Pro Leu Ala Leu Pro Tyr Asp Asn Thr Ser Cys Ser Asn Ser
             260                 265                 270

Thr Phe Phe Phe Asn Cys Ser Asn Cys Ser Cys Leu Ile Thr Pro Pro
         275                 280                 285

Phe Leu Val Gln Pro Phe Asn Phe Thr His Ser Val Cys Leu Tyr Ala
 290                 295                 300

Asp Tyr Gln Asn Asn Ser Phe Asp Ile Asp Val Gly Leu Ala Gly Phe
 305                 310                 315                 320

Thr Asn Cys Ser Ser Tyr Ile Asn Ile Ser Lys Pro Ser Ser Pro Leu
                 325                 330                 335

Cys Ala Pro Asn Ser Ser Val Phe Val Cys Gly Asn Asn Lys Ala Tyr
             340                 345                 350

Thr Tyr Leu Pro Thr Asn Trp Thr Gly Ser Cys Val Leu Ala Thr Leu
         355                 360                 365

Leu Pro Asp Ile Asp Ile Ile Pro Gly Ser Glu Pro Val Pro Ile Pro
 370                 375                 380

Ala Ile Asp His Phe Leu Gly Arg Pro Lys Arg Ala Ile Gln Phe Ile
 385                 390                 395                 400

Pro Leu Val Ile Gly Leu Gly Ile Thr Thr Ala Val Ser Thr Gly Thr
                 405                 410                 415

Ala Gly Leu Gly Val Ser Leu Thr Gln Tyr Thr Lys Leu Ser His Gln
             420                 425                 430

Leu Ile Ser Asp Val Gln Ala Ile Ser Ser Thr Ile Gln Asp Leu Gln
         435                 440                 445
```

```
Asp Gln Val Asp Ser Leu Ala Glu Val Val Leu Gln Asn Arg Arg Gly
    450                 455                 460
Leu Asp Leu Leu Thr Ala Glu Gln Gly Gly Ile Cys Leu Ala Leu Gln
465                 470                 475                 480
Glu Lys Cys Cys Phe Tyr Ala Asn Lys Ser Gly Ile Val Arg Asp Lys
                485                 490                 495
Ile Lys Asn Leu Gln Asp Asp Leu Glu Lys Arg Arg Lys Gln Leu Ile
            500                 505                 510
Asp Asn Pro Phe Trp Thr Gly Phe His Gly Leu Leu Pro Tyr Val Met
        515                 520                 525
Pro Leu Leu Gly Pro Leu Leu Cys Leu Leu Val Leu Ser Phe Gly
    530                 535                 540
Pro Ile Ile Phe Asn Lys Leu Met Thr Phe Ile Lys His Gln Ile Glu
545                 550                 555                 560
Ser Ile Gln Ala Lys Pro Ile Gln Val His Tyr His Arg Leu Glu Gln
                565                 570                 575
Glu Asp His Gly Gly Ser Tyr Leu Asn Leu Thr
            580                 585

<210> SEQ ID NO 80
<211> LENGTH: 574
<212> TYPE: PRT
<213> ORGANISM: Simian retrovirus SRV-2

<400> SEQUENCE: 80

Met Thr Leu Lys Asp Ile Pro Phe Trp Arg Val Leu Leu Ile Phe Gln
1               5                   10                  15
Thr Ala Arg Val Tyr Ala Gly Phe Gly Asp Pro Arg Glu Ala Ile Thr
            20                  25                  30
Met Ile His Gln Gln His Gly Lys Pro Cys Asp Cys Ala Gly Gly Tyr
        35                  40                  45
Val Asn Ala Ala Pro Thr Val Tyr Leu Ala Ala Val Ser Cys Ser Ser
    50                  55                  60
His Thr Ala Tyr Gln Pro Ser Asp Ser Leu Lys Trp Arg Cys Val Ser
65                  70                  75                  80
Asn Pro Thr Leu Ala Asn Gly Glu Asn Ile Gly Asn Cys Pro Cys Lys
                85                  90                  95
Thr Phe Lys Glu Ser Val His Ser Ser Cys Tyr Thr Ala Tyr Gln Glu
            100                 105                 110
Cys Phe Phe Gly Asn Lys Thr Tyr Tyr Thr Ala Ile Leu Ala Ser Asn
        115                 120                 125
Arg Ala Pro Thr Ile Gly Thr Ser Asn Val Pro Thr Val Leu Gly Asn
    130                 135                 140
Thr His Asn Leu Leu Ser Ala Gly Cys Thr Gly Asn Val Gly Gln Pro
145                 150                 155                 160
Ile Cys Trp Asn Pro Lys Ala Pro Val His Ile Ser Asp Gly Gly Gly
                165                 170                 175
Pro Gln Asp Lys Ala Arg Glu Ile Ala Val Gln Lys Arg Leu Glu Glu
            180                 185                 190
Ile His Lys Ser Leu Phe Pro Glu Leu Arg Tyr His Pro Leu Ala Leu
        195                 200                 205
Pro Lys Ala Arg Gly Lys Glu Lys Ile Asp Ala Gln Thr Phe Asn Leu
    210                 215                 220
Leu Thr Ala Thr Tyr Ser Leu Leu Asn Lys Ser Asn Pro Asn Leu Ala
225                 230                 235                 240
```

```
Asn Glu Cys Trp Leu Cys Leu Pro Ser Gly Asn Pro Ile Pro Leu Ala
            245                 250                 255

Ile Pro Ser Asn Asp Ser Phe Leu Gly Ser Asn Leu Ser Cys Pro Ile
        260                 265                 270

Ile Pro Pro Leu Leu Val Gln Pro Leu Glu Phe Met Asn Leu Ile Asn
    275                 280                 285

Ala Ser Cys Phe Tyr Ser Pro Phe Gln Asn Asn Ser Phe Asp Val Asp
290                 295                 300

Val Gly Leu Val Glu Phe Ala Asn Cys Ser Thr Thr Leu Asn Ile Ser
305                 310                 315                 320

His Ser Leu Cys Ala Pro Asn Ser Ser Val Phe Val Cys Gly Asn Asn
                325                 330                 335

Lys Ala Tyr Thr Tyr Leu Pro Ser Asn Trp Thr Gly Thr Cys Val Leu
            340                 345                 350

Ala Thr Leu Leu Pro Asp Ile Asp Ile Val Pro Gly Asp Ala Pro Val
        355                 360                 365

Pro Val Pro Ala Ile Asp His Tyr Leu His Arg Ala Arg Arg Ala Val
    370                 375                 380

Gln Phe Ile Pro Leu Leu Val Gly Leu Gly Ile Thr Thr Ala Val Ser
385                 390                 395                 400

Thr Gly Thr Ala Gly Leu Gly Tyr Ser Ile Thr Gln Tyr Thr Lys Leu
                405                 410                 415

Ser Arg Gln Leu Ile Ser Asp Val Gln Ala Ile Ser Ser Thr Ile Gln
            420                 425                 430

Asp Leu Gln Asp Gln Val Asp Ser Leu Ala Glu Val Val Leu Gln Asn
        435                 440                 445

Arg Arg Gly Leu Asp Leu Leu Thr Ala Glu Gln Gly Gly Ile Cys Leu
    450                 455                 460

Ala Leu Gln Glu Lys Cys Cys Phe Tyr Ala Asn Lys Ser Gly Ile Val
465                 470                 475                 480

Arg Asp Lys Ile Lys Arg Leu Gln Glu Asp Leu Glu Lys Arg Arg Lys
                485                 490                 495

Glu Ile Ile Asp Asn Pro Phe Trp Thr Gly Leu His Gly Leu Leu Pro
            500                 505                 510

Tyr Leu Leu Pro Leu Leu Gly Pro Leu Phe Cys Leu Leu Leu Leu Ile
        515                 520                 525

Thr Phe Gly Pro Leu Ile Phe Asn Lys Ile Ile Thr Phe Val Lys Gln
    530                 535                 540

Gln Ile Asp Ala Ile Gln Ala Lys Pro Ile Gln Val His Tyr His Arg
545                 550                 555                 560

Leu Glu Gln Glu Asp Asn Gly Gly Val Tyr Leu Arg Val Ser
                565                 570

<210> SEQ ID NO 81
<211> LENGTH: 586
<212> TYPE: PRT
<213> ORGANISM: Mason-Pfizer monkey virus

<400> SEQUENCE: 81

Met Asn Phe Asn Tyr His Phe Ile Trp Ser Leu Val Ile Leu Ser Gln
1               5                   10                  15

Ile Ser Gln Val Gln Ala Gly Phe Gly Asp Pro Arg Glu Ala Leu Ala
            20                  25                  30

Glu Ile Gln Gln Lys His Gly Lys Pro Cys Asp Cys Ala Gly Gly Tyr
        35                  40                  45
```

-continued

Val Ser Ser Pro Pro Ile Asn Ser Leu Thr Thr Val Ser Cys Ser Thr
 50                  55                      60

His Thr Ala Tyr Ser Val Thr Asn Ser Leu Lys Trp Gln Cys Val Ser
 65                  70                  75                  80

Thr Pro Thr Thr Pro Ser Asn Thr His Ile Gly Ser Cys Pro Gly Glu
                 85                  90                  95

Cys Asn Thr Ile Ser Tyr Asp Ser Val His Ala Ser Cys Tyr Asn His
                100                 105                 110

Tyr Gln Gln Cys Asn Ile Gly Asn Lys Thr Tyr Leu Thr Ala Thr Ile
                115                 120                 125

Thr Gly Asp Arg Thr Pro Ala Ile Gly Asp Gly Asn Val Pro Thr Val
130                 135                 140

Leu Gly Thr Ser His Asn Leu Ile Thr Ala Gly Cys Pro Asn Gly Lys
145                 150                 155                 160

Lys Gly Gln Val Val Cys Trp Asn Ser Arg Pro Ser Val His Ile Ser
                165                 170                 175

Asp Gly Gly Gly Pro Gln Asp Lys Ala Arg Asp Ile Ile Val Asn Lys
                180                 185                 190

Lys Phe Glu Glu Leu His Arg Ser Leu Phe Pro Glu Leu Ser Tyr His
                195                 200                 205

Pro Leu Ala Leu Pro Glu Ala Arg Gly Lys Glu Lys Ile Asp Ala His
210                 215                 220

Thr Leu Asp Leu Leu Ala Thr Val His Ser Leu Leu Asn Ala Ser Gln
225                 230                 235                 240

Pro Ser Leu Ala Glu Asp Cys Trp Leu Cys Leu Gln Ser Gly Asp Pro
                245                 250                 255

Val Pro Leu Ala Leu Pro Tyr Asn Asp Thr Leu Cys Ser Asn Phe Ala
                260                 265                 270

Cys Leu Ser Asn His Ser Cys Pro Leu Thr Pro Pro Phe Leu Val Gln
                275                 280                 285

Pro Phe Asn Phe Thr Asp Ser Asn Cys Leu Tyr Ala His Tyr Gln Asn
                290                 295                 300

Asn Ser Phe Asp Ile Asp Val Gly Leu Ala Ser Phe Thr Asn Cys Ser
305                 310                 315                 320

Ser Tyr Tyr Asn Val Ser Thr Ala Ser Lys Pro Ser Asn Ser Leu Cys
                325                 330                 335

Ala Pro Asn Ser Ser Val Phe Val Cys Gly Asn Asn Lys Ala Tyr Thr
                340                 345                 350

Tyr Leu Pro Thr Asn Trp Thr Gly Ser Cys Val Leu Ala Thr Leu Leu
                355                 360                 365

Pro Asp Ile Asp Ile Ile Pro Gly Ser Glu Pro Val Pro Ile Pro Ala
                370                 375                 380

Ile Asp His Phe Leu Gly Lys Ala Lys Arg Ala Ile Gln Leu Ile Pro
385                 390                 395                 400

Leu Phe Val Gly Leu Gly Ile Thr Thr Ala Val Ser Thr Gly Ala Ala
                405                 410                 415

Gly Leu Gly Val Ser Ile Thr Gln Tyr Thr Lys Leu Ser His Gln Leu
                420                 425                 430

Ile Ser Asp Val Gln Ala Ile Ser Ser Thr Ile Gln Asp Leu Gln Asp
                435                 440                 445

Gln Val Asp Ser Leu Ala Glu Val Val Leu Gln Asn Arg Arg Gly Leu
450                 455                 460

```
Asp Leu Leu Thr Ala Glu Gln Gly Gly Ile Cys Leu Ala Leu Gln Glu
465                 470                 475                 480

Lys Cys Cys Phe Tyr Ala Asn Lys Ser Gly Ile Val Arg Asp Lys Ile
            485                 490                 495

Lys Asn Leu Gln Asp Asp Leu Glu Arg Arg Arg Gln Leu Ile Asp
        500                 505                 510

Asn Pro Phe Trp Thr Ser Phe His Gly Phe Leu Pro Tyr Val Met Pro
        515                 520                 525

Leu Leu Gly Pro Leu Leu Cys Leu Leu Val Leu Ser Phe Gly Pro
    530                 535                 540

Ile Ile Phe Asn Lys Leu Met Thr Phe Ile Lys His Gln Ile Glu Ser
545                 550                 555                 560

Ile Gln Ala Lys Pro Ile Gln Val His Tyr His Arg Leu Glu Gln Glu
            565                 570                 575

Asp Ser Gly Gly Ser Tyr Leu Thr Leu Thr
            580                 585

<210> SEQ ID NO 82
<211> LENGTH: 4
<212> TYPE: PRT
<213> ORGANISM: Artificial Sequence
<220> FEATURE:
<223> OTHER INFORMATION: mutated cleavage site

<400> SEQUENCE: 82

Ala Ala Ala Arg
1

<210> SEQ ID NO 83
<211> LENGTH: 4
<212> TYPE: PRT
<213> ORGANISM: Artificial Sequence
<220> FEATURE:
<223> OTHER INFORMATION: spacer arm

<400> SEQUENCE: 83

Gly Gly Gly Ser
1

<210> SEQ ID NO 84
<211> LENGTH: 9
<212> TYPE: PRT
<213> ORGANISM: Artificial Sequence
<220> FEATURE:
<223> OTHER INFORMATION: C-terminal polyhistidine tail

<400> SEQUENCE: 84

Arg Gly Ser His His His His His His
1               5

<210> SEQ ID NO 85
<211> LENGTH: 19
<212> TYPE: PRT
<213> ORGANISM: Artificial Sequence
<220> FEATURE:
<223> OTHER INFORMATION: peptide

<400> SEQUENCE: 85

Thr Gly Met Ser Asp Gly Gly Val Gln Asp Gln Ala Arg Glu Lys
1               5                   10                  15

His Val Cys
```

METHODS FOR PRODUCING PEPTIDES INCLUDING HERV-W ENVELOPE MOTIFS AND FOR PRODUCING ANTIBODIES SPECIFIC FOR THE PEPTIDES

This is a continuation of application Ser. No. 12/087,893 filed Oct. 20, 2008, which is a National Stage Application of PCT/FR2007/000236 filed Feb. 9, 2007, and claims the benefit of French Application No. 06 50468 filed Feb. 9, 2006. The entire disclosures of the prior applications are hereby incorporated by reference in their entirety.

The present invention relates to a polypeptide domain responsible for interactions between a retroviral envelope of the HERV-W interference group and the receptors of the hASCT family.

BACKGROUND

Human endogenous retroviruses (HERVs) constitute 8% of the human genome and are involved both in pathologies and in nonpathological phenomena.

The human endogenous retrovirus family W (HERV-W) is derived from an infectious retroviral element that was integrated into the germ line 25 to 40 million years ago. The HERV-W envelope protein, also called syncytin, is a fusogenic glycoprotein involved in the formation of the syncytiotrophoblastic layer of the placenta. It is encoded by the env gene of the proviral locus ERVW1 and synthesized in the form of a gPr73 precursor which is specifically cleaved into two mature proteins, a surface subunit gp50 (SU) and a transmembrane subunit gp24 (TM).

In vitro, syncytin of the HERV-W family induces a cell to cell fusion that is dependent on its interaction with a receptor-transporter of amino acids of the ASCT family (h-ASCT2, hASCT1). Phylogenic studies then showed that syncytin is related to a group of retroviruses comprising in particular the cat endogenous virus RD114, the monkey endogenous virus BaEV, simian retroviruses and avian retroviruses: avian reticuloendotheliosis virus REV-A and spleen necrosis virus SNV, all having in common the type 2 sodium-dependant neutral amino acid receptor-transporter or hASCT2 (Rasko et al, 1999, Proc. Natl. Acad. Sci. USA Vol. 96, pp. 2129-2134; Tailor et al, 1999 Journal of Virology, vol. 73(5) May 1999, P. 4470-4474). Thus, the infection of cells with viruses of this retrovirus group leads to a specific reduction in the transport of amino acids (Rasko et al., 1999). The infection of a cell with one of these retroviruses (or the expression of one of these envelopes in the cell) prevents, through interference (interaction) in relation to a receptor of the ASCT family, the infection of this same cell by another of these retroviruses or the fusion with another cell expressing another envelope. Through interference in relation to a receptor of the ASCT family, the infection of a cell by one of these retroviruses prevents the infection by another of these retroviruses. All these retroviruses belong to the same HERV-W virus interference group.

The mechanisms of binding between the envelope and the ASCT receptor remain obscure, and to date no domain for binding to an ASCT receptor has been identified and defined either in the SU of the HERV-W envelope protein or in the SUs of retroviruses of the same interference group. This theme is nevertheless essential since the inhibition of the envelope/ASCT receptor interaction would in addition make it possible to prevent the entry of a retrovirus into the cell, and therefore to block its replication cycle, to block the phenomenon of envelope/ASCT receptor interaction and/or of cell fusion which may be involved in the formation of tumors, in the proliferation of metastasic cells or in drug resistance phenomena (see by way of illustration the publication "Cell fusion: A hidden enemy?, Cancer Cell: May 2003, vol. 3), to block the phenomenon of envelope/ASCT receptor interaction and/or of cell fusion which may be involved in nervous system diseases and even to inhibit the cell-cell fusion involved in trophoblastic differentiation (contraceptive vaccination). Furthermore, the inhibition of the envelope/hASCT receptor interaction could prevent tumor propagation by counteracting a local immunosuppression which may result from the envelope/hASCT receptor interaction. Indeed, it has been shown, on the one hand, that the infection of cells with viruses of this retrovirus group (in particular those inducing immunodeficiencies) leads to a specific reduction in the transport of amino acids (Rasko et al, PNAS, vol. 96. pp 2129-2134 (1999)), and on the other hand, a direct link is proposed between the impairment of the transport of amino acids and immunosuppression (Espinosa A, Villarreal L P., T-Ag inhibits implantation by EC cell derived embryoid bodies. Virus Genes. 2000; 20(3): 195-200; JE, Battini J L, Gottschalk R J, Mazo I, Miller A D., The RD114/simian type D retrovirus receptor is a neutral amino acid transporter. Proc Natl Acad Sci USA, 1999, Mar. 2; 96(5): 2129-34). Thus, as regards nervous system diseases, it is known that the hASCT receptors are involved in the specific transport of neutral amino acids and that neuronal cells, for the transmission of information, predominantly use neuromediators of a polypeptide nature. Thus, the binding of the Env-HERV-W protein to receptors which normally have to transport the amino acids required for the synthesis of neuromediators can affect the capacity of the neurons to synthesize the neuromediators by reducing the entry of the physiological agonists such as amino acids via the ASCT receptors. Moreover, if neurons whose intercellular networks form connections which are essential for the transmission of information circulating in the brain and the spinal cord, form syncytia following a fusion of several neurons which is induced by the Env-HERV-W protein, all the networks for transmission of information become disrupted and connected to the same fused "cellular package" and, furthermore, the neuromediator production activity of each cell is no longer individualized or connected to the upstream or downstream conduction pathways (dendrites and axons) which are specific to it.

SUMMARY

Surprisingly, the inventors have identified the polypeptide region responsible for the interactions between the envelope of a virus belonging to the HERV-W interference group and an hASCT receptor.

To this effect, the present invention relates to a peptide domain necessary for the interaction between the envelope of a virus belonging to the HERV-W interference group and an hASCT receptor, defined in that it starts with an N-terminus and ends with a C-terminus, and in that:
  the N-terminus is defined by a motif, consisting of the amino acids $(Z)_\alpha$-proline-cysteine-X-cysteine
    in which
    Z is any amino acid
    $\alpha$ is an integer between 2 and 30
    X is any amino acid,
    said motif being chosen from SEQ ID NO: 1 to SEQ ID NO: 29 and SEQ ID NO: 44 to SEQ ID NO: 72 the C-terminus is defined by a motif consisting of the amino acids serine-aspartic acid-$X_a$-$X_b$-$X_c$-$X_d$-$X_e$ aspartic acid-$X_f$-$X_g$-$(Z)_\beta$ in which $X_a$, $X_b$, $X_c$, $X_d$, $X_e$, $X_f$, $X_g$ are any amino acids Z is any amino acid $\beta$ is an integer between 15 and 25, preferably 20 said motif being chosen from SEQ ID NO: 30 to SEQ ID NO: 40, and in that said peptide domain comprises, between the N-terminus and the C-terminus, at least one motif chosen from the following motifs:

a motif consisting of the amino acids cysteine-tyrosine-$X_2$-$X_3$-$X_4$-$X_5$-$X_6$-cysteine, in which $X_2$, $X_3$, $X_4$, $X_5$, $X_6$ are any amino acids said motif corresponding to SEQ ID NO: 41 a motif consisting of the amino acids cysteine-$X_7$-$X_8$-$X_9$-$X_{10}$-$X_{11}$-$X_{12}$-$X_{13}$-$X_{14}$-$X_{15}$-cysteine-tryptophan, in which $X_7$, $X_8$, $X_9$, $X_{10}$, $X_{11}$, $X_{12}$, $X_{13}$, $X_{14}$, $X_{15}$ are any amino acids said motif corresponding to SEQ ID NO: 42 or SEQ ID NO: 73.

DETAILED DESCRIPTION OF EMBODIMENTS

The expression peptide domain according to the invention is understood to mean a minimum region of the envelope of a virus of the HERV-W interference group necessary for the recognition of an hASCT receptor.

The peptide domains of the invention may be obtained by the genetic engineering technique which comprises the steps of:

culturing a microorganism or eukaryotic cells transformed with the aid of a nucleotide sequence according to the invention, and recovering the peptide domain produced by said microorganism or said eukaryotic cells.

This technique is well known to a person skilled in the art. For further details concerning it, reference may be made to the book below: Recombinant DNA Technology I, Editors Ales Prokop, Raskesh K Bajpai; Annals of the New York Academy of Sciences, Volume 646, 1991. The peptide domains of the invention may also be prepared by conventional peptide syntheses well known to a person skilled in the art.

The expression interference group is understood to mean all the viruses for which the infection (expression) of a cell by one of its members prevents infection by another member of the group by receptor interference.

The expression any amino acid is understood to mean in particular an amino acid chosen from arginine, histidine, lysine, aspartic acid, glutamic acid, asparagine, glutamine, serine, threonine, asparagine, threonine, alanine, isoleucine, leucine, methionine, phenylalanine, tryptophan, tyrosine, valine, cysteine, glycine, proline.

The expression hASCT receptor is understood to mean any sodium-dependent neutral amino acid transporter.

The expression motifs is understood to mean a succession of amino acids corresponding to a particular region of interest of the peptide domain according to the invention, which is expressed by all the viruses of the HERV-W virus interference group.

Preferably, $\alpha$ is an integer between 3 and 18.

Preferably X or Xaa of the Pro Cys Xaa Cys motif in SEQ ID NO: 1 to SEQ ID NO: 29 is an amino acid chosen from aspartic acid, glutamic acid, arginine: these sequences are those preferably chosen from SEQ ID NO: 44 to SEQ ID NO: 72.

Preferably, $X_a$, $X_b$, $X_c$ or the amino acids at positions 3, 4 and 5 of SEQ ID NOS: 30 to 40 are a glycine, $X_d$ or the amino acid Xaa at position 6 of SEQ ID NOS: 30 to 40 is an amino acid chosen from proline and valine; $X_e$ or the amino acid Xaa at position 7 of SEQ ID NOS: 30 to 40 is an amino acid chosen from glutamine, leucine and threonine; $X_f$ or the amino acid Xaa at position 9 of SEQ ID NOS: 30 to 40 is an amino acid chosen from lysine, threonine, methionine and glutamine, $X_g$ or the amino acid at position 10 of SEQ ID NOS: 30 to 40 is an amino acid chosen from alanine, lysine, isoleucine, threonine and valine.

Preferably, $\beta$ is an integer equal to 20.

Preferably, $X_2$ or the amino acid Xaa at position 3 of SEQ ID NO: 41 is an amino acid chosen from asparagine, threonine, glutamic acid, histidine, $X_3$ or the amino acid Xaa at position 4 of SEQ ID NO: 41 is an amino acid chosen from histidine, alanine, serine, lysine, glutamic acid; $X_4$ or the amino acid Xaa at position 5 of SEQ ID NO: 41 is an amino acid chosen from tyrosine, threonine, alanine, $X_5$ or the amino acid Xaa at position 6 of SEQ ID NO: 41 is an amino acid chosen from glutamine, arginine, threonine, $X_6$ or the amino acid Xaa at position 7 of SEQ ID NO: 41 is an amino acid chosen from leucine, glutamine, glutamic acid.

Preferably $X_7$ or the amino acid Xaa at position 2 of SEQ ID NO: 42 is an amino acid chosen from proline, threonine, arginine and asparagine; $X_8$ or the amino acid Xaa at position 3 of SEQ ID NO: 42 is an amino acid chosen from glycine, glutamic acid, asparagine, $X_9$ or the amino acid Xaa at position 4 of SEQ ID NO: 42 is an amino acid chosen from glycine, asparagine, isoleucine, threonine, serine, $X_{10}$ or the amino acid Xaa at position 5 of SEQ ID NO: 42 is lysine or is deleted; $X_{11}$ or the amino acid Xaa at position 6 of SEQ ID NO: 42 is an amino acid chosen from lysine, valine, isoleucine, leucine, $X_{12}$ or the amino acid Xaa at position 7 of SEQ ID NO: 42 is an amino acid chosen from glycine, asparagine; $X_{13}$ or the amino acid Xaa at position 8 of SEQ ID NO: 42 is an amino acid chosen from glutamine, lysine, valine, $X_{14}$ or the amino acid Xaa at position 9 of SEQ ID NO: 42 is an amino acid chosen from valine, proline, serine, threonine, $X_{15}$ or the amino acid Xaa at position 10 of SEQ ID NO: 42 is an amino acid chosen from valine, isoleucine.

Preferably, the amino acid Xaa at position 2 of SEQ ID NO: 73 is chosen from proline, threonine, arginine and asparagine, the amino acid Xaa at position 3 of SEQ ID NO: 73 is chosen from glycine, glutamic acid, asparagine, the amino acid Xaa at position 4 of SEQ ID NO: 73 is chosen from glycine, asparagine, isoleucine, threonine, serine, the amino acid Xaa at position 5 of SEQ ID NO: 73 is chosen from lysine, valine, isoleucine, leucine, the amino acid Xaa at position 6 of SEQ ID NO: 73 is chosen from glycine, asparagine, the amino acid Xaa at position 7 of SEQ ID NO: 73 is chosen from glutamine, lysine, valine, the amino acid Xaa at position 8 of SEQ ID NO: 73 is chosen from valine, proline, serine, threonine, the amino acid Xaa at position 9 of SEQ ID NO: 73 is chosen from valine, isoleucine.

Deletions are possible in the domains according to the invention indicated above. According to a particular embodiment of the invention, $X_{10}$ is deleted.

The invention also relates to a nucleotide sequence encoding a peptide domain according to the invention above.

Such sequences may be prepared by chemical synthesis and genetic engineering using techniques well known to a person skilled in the art and described, for example, in Sambrook, J. et al., Molecular Cloning: A Laboratory Manual, 1989.

The invention also relates to an epitope derived from the peptide domain according to the invention, characterized in that it induces an immune response against a virus belonging to the HERV-W interference group.

The expression epitope is understood to mean all or part of the peptide domain according to the invention recognized by a receptor located at the surface of a B or T lymphocyte or of a circulating antibody.

The expression immune response is understood to mean all the biological mechanisms which allow a pluricellular organism to maintain the coherence of the cells and tissues which constitute it and to ensure its integrity in response to any attack which modifies the molecular structures of its constituents or which introduces foreign molecules into the organism.

The invention also relates to a nucleotide sequence encoding an epitope as defined above. As indicated above, such sequences may be prepared by chemical synthesis and genetic engineering using techniques well known to a person skilled in the art and described, for example, in Sambrook J. et al., Molecular Cloning: A Laboratory Manual, 1989.

The invention also relates to an expression vector characterized in that it comprises a nucleotide sequence according to the invention, and the means necessary for its expression.

By way of expression vector, there may be mentioned, for example, plasmids, viral vectors of the vaccinia virus, adenovirus, baculovirus, poxvirus or retrovirus type, bacterial vectors of the *salmonella* or BCG type.

The expression means necessary for its expression is understood to mean any means which make it possible to obtain a peptide from a nucleotide sequence, such as in particular a promoter, a transcription terminator, a replication origin and preferably a selectable marker.

The vectors of the invention may also comprise sequences necessary for targeting peptides to particular cell compartments.

The invention also relates to a host microorganism or cell transformed with at least one expression vector according to the invention.

By way of examples of microorganisms which are suitable for the purposes of the invention, there may be mentioned yeasts, such as those of the following families: *Saccharomyces, Schizosaccharoyces, Kluveromyces, Pichia, Hanseluna, Yarowia, Schwaniomyces, Zygosaccharomyces; Saccharomyces cerevisiae, Saccharomyces carlsbergensis* and *Kluveromyces lactis* being preferred; and bacteria such as *E. coli* and those of the following families: *Lactobacillus, Lactococcus, Salmonella, Streptococcus, Bacillus* and *Streptomyces*.

By way of examples of transformed host cells, there may be mentioned cells derived from animals such as mammals, reptiles, insects and the like. The preferred eukaryotic cells are cells derived from the Chinese hamster (CHO cells), from monkeys (COS and Vero cells), from young hamster kidney (BHK cells), from pig kidney (PK 15 cells) and from rabbit kidney (RK13 cells), human osteosarcoma cell lines (143 B cells), human HeLa cell lines and human hepatoma cell lines (of the Hep G2 cell type), and insect cell lines (for example *Spodoptera frugiperda*), a human embryonic kidney cell line (for example HEK293T). The host cells may be provided in cultures in suspension or in flasks, in tissue cultures, organ cultures and the like.

The invention also relates to an antibody directed against a peptide domain according to the invention or against an epitope according to the invention.

The expression antibody is understood to mean both a whole antibody and an antibody fragment.

The recombinant antibodies may be obtained according to conventional methods known to a person skilled in the art, from prokaryotic organisms, such as bacteria, or from eukaryotic organisms, such as yeasts, mammalian, plant, insect or animal cells, or by extracellular production systems.

The monoclonal antibodies may be prepared according to conventional techniques known to a person skilled in the art such as the hybridoma technique whose general principle is recalled below.

In a first instance, an animal, generally a mouse (or cultured cells in the context of in vitro immunizations), is immunized with a target antigen of interest, whose B lymphocytes are then capable of producing antibodies against said antigen. These antibody-producing lymphocytes are then fused with "immortal" myelomatous cells (murine in the example) in order to give rise to hybridomas. From the heterogenous mixture of cells thus obtained, a selection of the cells capable of producing a particular antibody and of multiplying it indefinitely is then carried out. Each hybridoma is multiplied in clone form, each leading to the production of a monoclonal antibody whose recognition properties in relation to the antigen of interest may be tested, for example by ELISA, by one- or two-dimensional immunotransfer, by immunofluorescence or with the aid of a biosensor. The monoclonal antibodies thus selected are subsequently purified in particular according to the affinity chromatography technique.

The expression antibody fragment is understood to mean any antibody fragment following an immune response against a virus belonging to the HERV-W interference group. These antibody fragments may, for example, be obtained by proteolysis. Thus, they may be obtained by enzymatic digestion, resulting in fragments of the Fab type (treatment with papain; Porter R R, 1959, Biochem. J., 73: 199-126) or of the F(ab)'$_2$ type (treatment with pepsin; Nisonoff A. et al., 1960, Science, 132: 1770-1771). They may also be prepared by the recombinant route (Skerra A., 1993, Curr. Opin. Immunol., 5: 256-262). Another antibody fragment which is suitable for the proposals of the invention comprises an Fv fragment which is a dimer consisting of the noncovalent combination of the variable light (VL) domain and of the variable heavy (VH) domain of the Fab fragment, and therefore the combination of two polypeptide chains. In order to improve the stability of the Fv fragment due to the dissociation of the two polypeptide chains, this Fv fragment may be modified by genetic engineering by inserting a suitable linker peptide between the VL domain and the VH domain (Huston P. et al., 1988, Proc. Natl. Acad. Sci. USA, 85: 5879-5883). The expression scFv fragment ("single chain Fragment variable") is then used because it consists of a single polypeptide chain. The use of a linker peptide preferably composed of 15 to 25 amino acids makes it possible to link the C-terminus of one domain to the N-terminus of the other domain, thus constituting a monomeric molecule endowed with binding properties similar to those of the antibody in its complete form. Both orientations of the VL and VH domains are suitable (VL-linker-VH and VH-linker-VL) because they exhibit identical functional properties. Of course, any fragment known to a person skilled in the art and exhibiting the immunological characteristics defined above are suitable for the purposes of the invention.

The invention also relates to the use of at least one peptide domain according to the invention, of at least one epitope according to the invention, of at least one antibody according to the invention or of at least one nucleotide sequence according to the invention, for the preparation of a medicament intended for the inhibition, prevention or treatment of an infection caused by a virus belonging to the HERV-W interference group in an animal, preferably humans. The peptide domain according to the invention may be used in particular for targeting cells expressing a receptor of the hASCT family in order to transduce a signal, and modulate the flow of amino acids (cancer treatments).

The expression elements necessary for a constitutive expression of peptides is understood to mean a ubiquitous promoter specific to eukaryotic cells. By way of elements necessary for an inducible expression of the peptides, there may be mentioned the elements for regulating the *E. coli* operon for resistance to tetracycline (Gossen M. et al., Proc. Natl. Acad. Sci. USA, 89: 5547-5551 (1992)).

The use of at least one peptide domain according to the invention, of at least one epitope according to the invention, or of at least one nucleotide sequence according to the invention is particularly suitable for the preparation of a medicament intended for the prevention of an infection caused by a virus belonging to the HERV-W interference group in an animal, preferably humans. The use of at least one antibody according to the invention is particularly suitable for the preparation of a medicament intended for the inhibition or treatment of an infection or a pathology induced by a virus belonging to the HERV-W interference group in an animal, preferably humans.

The invention also relates to a pharmaceutical composition comprising, by way of active substance, at least one peptide domain according to the invention, at least one epitope according to the invention, or alternatively at least one of the nucleotide sequences according to the invention, in particular placed under the control of elements necessary for a constitutive and/or inducible expression of said peptide domains or epitopes, in combination with a pharmaceutically appropriate vehicle. The invention also relates to a pharmaceutical composition comprising, by way of active substance, at least one antibody according to the invention, in combination with a pharmaceutically appropriate vehicle.

Of course, persons skilled in the art will easily determine the pharmaceutically appropriate vehicle and the quantity of peptide domains, of epitopes, of nucleotide acids or of antibodies to be used according to the constituents of the pharmaceutical composition.

In the pharmaceutical compositions according to the invention, for oral, sublingual, subcutaneous, intramuscular, intravenous, topical, intratracheal, rectal or transdermal administration, the active substance may be administered in unit forms for administration or as a mixture with conventional pharmaceutical supports and intended for administration by the oral route, for example in the form of a tablet, a gelatin capsule, an oral solution, and the like, or by the rectal route, in the form of a suppository, or by the parenteral route, in particular in the form of a solution for injection, in particular by the intravenous, intradermal or subcutaneous route, and the like, according to conventional protocols well known to persons skilled in the art. For topical application, the active substance may be used in creams, ointments, lotions, eyedrops.

When a solid composition in tablet form is prepared, the active substance is mixed with the pharmaceutically acceptable excipient, also called a pharmaceutical vehicle, such as gelatin, starch, lactose, magnesium stearate, talc, gum Arabic or the like. The tablets may be coated with sucrose, with a cellulose derivative or with other appropriate materials. It is also possible to treat them such that they have a prolonged or delayed activity and they continuously release a predetermined quantity of the active substance. It is also possible to obtain a preparation as gelatin capsules by mixing the active substance with a diluent and pouring the mixture into soft or hard gelatin capsules. It is also possible to obtain a preparation in syrup form or for administration in the form of drops, in which the active substance is present together with a sweetener, an antiseptic, such as in particular methylparaben and propylparaben, and a taste enhancer or an appropriate colorant. The powders or water-dispersible granules may contain the active substance in the form of a mixture with dispersing agents or wetting agents, or suspending agents, well known to persons skilled in the art. For parentral administration, aqueous suspensions, isotonic saline solutions or sterile solutions or solutions for injection which contain dispersing agents, pharmacologically compatible wetting agents, such as in particular polyethylene glycol or butylene glycol, are used.

The medicament or the pharmaceutical composition according to the invention may additionally comprise an activating agent which induces the effects of a medication or reinforces or supplements the effects of the principal medication, by increasing in particular the bioavailability of the principal medication.

The dosage depends on the seriousness of the condition and will be adapted according to a conventional protocol. As a guide, when the active substance is a monoclonal antibody, the weekly dose is from 1 to 10 mg/kg, in combination with a pharmaceutically acceptable excipient.

The invention also relates to a diagnostic composition for the detection and/or quantification of a virus belonging to the HERV-W interference group, or the detection and/or quantification of an immune response against said virus, comprising at least one peptide domain according to the invention, at least one epitope according to the invention, at least one of the nucleotide sequences according to the invention, or at least one antibody according to the invention.

A diagnostic composition comprising at least one peptide domain according to the invention, at least one epitope according to the invention, at least one of the nucleotide sequences according to the invention, is particularly suitable if it is desired to determine if a patient has an immune response against a virus belonging to the HERV-W interference group while a diagnostic composition comprising at least one antibody according to the invention is particularly suitable for the detection and/or quantification of a virus belonging to the HERV-W interference group.

The invention also relates to a method for the detection and/or quantification of a virus belonging to the HERV-W interference group in a biological sample taken from an individual liable to be infected by said virus, characterized in that it comprises the steps consisting in:
 bringing said biological sample into contact with at least one antibody according to the invention under conditions allowing the formation of a complex between the virus and the antibody, and
 detecting and/or quantifying the formation of said complex by any appropriate means.

The expression biological sample is understood to mean a biological sample of human or animal origin liable to contain said virus, such as a sample of blood, plasma, serum, urine, cerebrospinal fluid, or of tissues, such as placenta, testicles, prostate and breast.

The step of bringing into contact is a step that is conventionally known to a person skilled in the art.

The detection/quantification step may be carried out by any detection means known in the field of immunological assays of very small molecules, such as direct detection, that is to say without the intermediary of a binding partner or of binding partners, and indirect detection, that is to say through the intermediary of a binding partner or of binding partners.

The direct detection of the binding between the antibody or antibody fragment of the invention and the virus may be carried out for example by surface plasmon resonance or by cyclic voltammetry on an electrode bearing a conducting polymer. In this case, the antibody of the invention serves to immunocapture all or part of the virus, which is then eluted. The elution may be carried out by any elution method known to a person skilled in the art, such as a pH shock.

In the case of indirect detection, the second step of the method of the invention may be carried out according to the conventional ELISA competition assay technique. The antibody of the invention then serves as binding partner serving to capture all or part of the virus in the sample. The detection may then be performed by competition between all or part of the virus which may be contained in the sample to be tested and a previously labeled known quantity of virus.

The expression labeling is understood to mean the attachment of a marker capable of directly or indirectly generating a detectable signal. A nonlimiting list of these markers consists of:

- enzymes which produce a detectable signal, for example, by colorimetry, fluorescence, luminescence, such as horseradish peroxidase, alkaline phosphatase, acetylcholine esterase, β-galactosidase, glucose-6-phosphate dehydrogenase,
- chromophores such as luminescent, coloring compounds,
- radioactive molecules such as 32P, 35S or 125I,
- fluorescent molecules such as fluorescein, rhodomine, alexa or phycocyanins, and
- particles such as gold or magnetic latex particles, liposomes.

Indirect labeling systems may also be used, such as, for example, via another ligand/anti-ligand pair. The ligand/anti-ligand pairs are well known to a person skilled in the art, and the following pairs may be mentioned for example: biotin/streptavidin, biotin/avidin, hapten/antibody, antigen/antibody, peptide/antibody, sugar/lectin, polynucleotide/complementary strand for the polynucleotide. In this case, it is the ligand which is bound to the binding partner. The anti-ligand may be detected directly by the markers described in the proceeding paragraph or may itself be detected by a ligand/anti-ligand.

These indirect systems may lead, under certain conditions, to an amplification of the signal. This signal amplification technique is well known to a person skilled in the art, and reference may be made to the previous patent applications FR98/10084 or WO95/08000 by the applicant or to the article J. Histochem. Cytochem., (1997), 45: 481-491.

The labeling of molecules is widely known to a person skilled in the art and is described for example by Greg T. Hermanson in Bioconjugate Techniques, 1996, Academic Press Inc., 525B Street, San Diego, Calif. 92101 USA.

Depending on the type of labeling used, such as for example using an enzyme, a person skilled in the art will add reagents which allow visualization of the labeling.

Such reagents are widely known to a person skilled in the art and are described in particular in Principles and Practice of Immunoessay, 2nd edition, Edited by C. Price, D. G. Newman, Stockton Press, 1997, 345 Park Avenue South, N.Y.

The invention also relates to the use of the above composition for the in vitro screening of a virus belonging to the HERV-W interference group in a biological sample or specimen. In particular, the early screening of a virus such as SRV1 and SRV2, viruses that are involved in immunodeficiency mechanisms in monkeys, makes it possible to provide a treatment suitable for the host before the appearance of an immunodeficiency. Moreover, the early screening of HERV-W, involved in placental pathologies, makes it possible to modulate its expression, for example, during a preeclampsia.

The invention also relates to the use of a peptide domain according to the invention or of an epitope according to the invention, or of an antibody according to the invention, for inhibiting the interaction between the envelope of a virus belonging to the HERV-W interference group and an ASCT receptor. This makes it possible, in particular, to obtain a contraceptive immunotherapy.

The invention also relates to the use of a peptide domain according to the invention for identifying chemical or biological molecules whose interaction with all or part of this peptide domain blocks the interaction between the envelope of a virus belonging to the HERV-W interference group and an ASCT receptor. For example, when a peptide domain according to the invention of HERV-W is used, this makes it possible to obtain in particular chemical or biological molecules that are highly suitable in order to obtain a contraceptive treatment. The use of such chemical molecules to inhibit the interaction between the envelope of a virus belonging to the HERV-W interference group and an ASCT receptor is of therapeutic interest.

As a guide, two generic methods allowing the screening of chemical or biological molecules capable of inhibiting the env/receptor interaction are described below.

In a context where it is possible to produce a soluble envelope, it is advisable to determine if a chemical or biological molecule alters the env/receptor interaction according to an ELISA type method using cells expressing at least one hASCT receptor in a capture phase. Thus, on a 96-well plate, cells expressing an hASCT receptor of interest are cultured or adsorbed, and an env/receptor interaction is detected via the use of a labeled soluble envelope (histine tag, GPF fusion), and therefore capable of generating a reference signal that can be assayed. If a signal reduction is observed after preincubation of said soluble envelope with a chemical or biological molecule, that means that the chemical or biological molecule alters the env/receptor interaction. Alternatively, it is possible to use a retroviral vector pseudotyped by the envelope of interest and expressing a detectable marker (LacZ) and to carry out the same test. It is also possible to select molecules of interest via a measurement of fusion inhibition. Cells expressing the receptor of interest (cell-recept), for example HeLa or XC-RDR cells, and cells constitutively expressing a marker (for example, LacZ) and transiently or stably expressing the envelope of interest (cell-env-LacZ) are used; the envelope of interest was modified beforehand at the level of its intracytoplasmic tail by exchange with the intracytoplasmic domain of HERV-W env so as to make it constitutively fusogenic (Cheynet et al, 79(9): 5586-5593, 2005). The bringing into contact of the two cell types, "cell-recept" in excess and "cell-env-LacZ" in insufficient amount, leads to the formation of multinucleated giant cells or syncytia, containing one or two blue nuclei derived from "cell-env-LacZ" and tens of white nuclei derived from "cell-recept". An identical co-culture performed in the presence of a chemical or biological molecule altering the env/receptor interaction leads to a reduction in the number of syncytia and their nucleus content. Automation of such measurements with the aid of a CCD camera is possible.

The invention also relates to the use of a peptide domain in accordance with the invention for generating antibodies blocking the interaction between the envelope of a virus belonging to the HERV-W interference group and an hASCT receptor.

The invention also relates to a method for determining a polypeptide region necessary for the interaction between the envelope of a virus belonging to the HERV-W interference group and an hASCT receptor, characterized in that:
the nucleotide and/or peptide sequence of the precursor envelope of said virus is identified
the signal part is excluded
a serine-aspartic acid-$X_a$-$X_b$-$X_c$-$X_d$-$X_e$-aspartic acid-$X_f$-$X_g$ is detected domain
in which
$X_a$, $X_b$, $X_c$, $X_d$, $X_e$, $X_f$, $X_g$, are any amino acids which correspond to SEQ ID NO: 43
the C-terminus is excluded between 15 and 25 amino acids, preferably 20 amino acids, after said serine-aspartic acid-$X_a$-$X_b$-$X_c$-$X_d$-$X_e$-aspartic acid-$X_f$-$X_g$ domain, which corresponds to SEQ ID NO: 43.

Preferably, $X_a$, $X_b$, $X_c$ is an amino acid which is glycine, $X_d$ is an amino acid chosen from proline and valine, $X_e$ is an amino acid chosen from glutamine, leucine and threonine, $X_f$ is an amino acid chosen from lysine, threonine, methionine and glutamine, $X_g$ is an amino acid chosen from alanine, lysine, isoleucine, threonine and valine.

For the purposes of the present invention, the nucleotide sequence and/or peptide consequent of the precursor envelope of said virus is identified by any means known to a person skilled in the art, who may refer in particular to Maniatis (ed. 1989).

The signal part is excluded by any means known to a person skilled in the art, as described in particular in "Improved Prediction of Signal Peptide: SignalP 3.0" Jannick Dyrløv Bendtsen, Henrik Nielsen, Gunnar von Hiejne and Søren Brunak, J. Mol. Biol., 340: 783-795, 2004.

Said domain is detected by any means known to a person skilled in the art, that is to say using Blast or Fasta type software (see, in particular, Altschul S F, Gish W, Miller W, Myers E W, Lipman D J., Basic local alignment search tool. J. Mol. Biol. 1990 Oct. 5; 215(3): 403-10).

The invention also relates to a peptide domain capable of being obtained by the above method.

BRIEF DESCRIPTION OF THE FIGURES

The accompanying figures are given by way of explanatory example and have no limiting character. They will make it possible to better understand the invention.

FIG. 1a illustrates the largest soluble recombinant protein comprising all or part of the SU and TM subunits (Env-Gp60) (in which the native cleavage site RNKR at positions 314 to 317 of SEQ ID NO: 75 between the SU and TM subunits was mutated to AAAR (SEQ ID NO: 82)) and the soluble recombinant protein corresponding to the SU subunit (EnvSU). FIG. 1b represents the flow cytometry analysis of the test for binding of the EnvSU recombinant protein to XC hASCT2 and XC hASCT1 cells expressing the hASCT2 and hASCT1 receptors, respectively. FIG. 1c illustrates the test of interference of binding to the TE671 cells (control hASCT2), TE671RD cells (blocked hASCT2) and TE671galv cells (blocked Pit1).

FIG. 2b represents the flow cytometry analysis of the test of binding of the recombinant proteins derived from EnvSU to the XC hASCT2 cells expressing the hASCT2 receptor, in particular the binding of the Env197, Env168 and Env144 mutants and the binding defect of the Env69-317, Env169-317 and Env117 mutants.

EXAMPLES

The following examples are given by way of illustration and have no limiting character. They will make it possible to better understand the invention.

Example 1: Molecular and Phenotypical Characterization of Recombinant Envelopes

Construction and Production of the HERV-W Envelope SU Subunit

A vector phCMVEnv-Gp60 allowing the expression of a soluble recombinant envelope protein was designed from the expression vector phCMV-Env-W (Blond J Virol, Vol 74(7): 3321-3329, 2000) containing the HERV-W envelope gene (538 amino acids) (clone PH74, Blond et al. J Virol Vol 73(2): 1175-1185, 1999).

The soluble envelope (Gp60,1-435) was constructed as described below:
(1) The native cleavage site RNKR (positions 314 to 317 of SEQ ID NO: 75) between the SU and TM subunits was mutated to AAAR (SEQ ID NO: 82) in order to allow the production of a fusion protein that was stable and not of two SU-TM subunits cleaved and then recombined by a disulfide bridge.

(2) The transmembrane (tm) and intracytoplasmic (CYT) regions corresponding to amino acids 436 to 538 were deleted in order to obtain a soluble protein.

(3) A spacer arm having the composition (GGGS)3 (SEQ ID NO: 83), followed by a polyhistidine tail (RGS-HHHHHH) (SEQ ID NO: 84), were added at the C-terminal position in order to allow the purification of this protein by IMAC and the detection by an anti-histidine monoclonal antibody (QIAGEN, RGS H6).

Starting with the vector phCMVEnv-Gp60 expressing the soluble envelope, the vector phCMV-EnvSU was constructed, allowing the production of an SU protein. The soluble SU is a fusion protein containing a C-terminal polyhistidine tail having the sequence RGS-HHHHHH (SEQ ID NO: 84) immediately downstream of the sequence AAAR (SEQ ID NO: 82), in order to allow the purification of this protein by IMAC and the detection by an anti-histidine monoclonal antibody (QIAGEN, RGS H6).

Figure 1A:
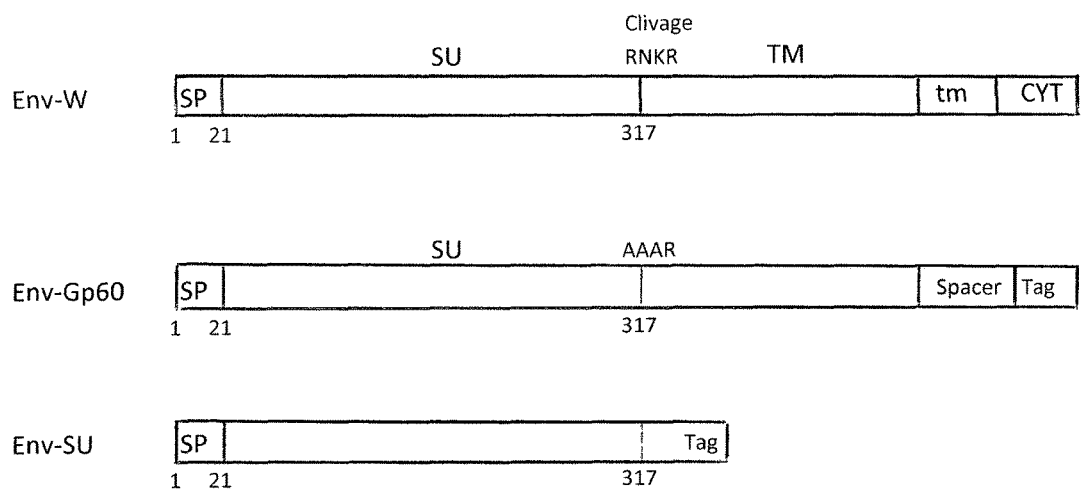
FIGS. 1a, 1b, and 1c illustrate the phenotypical characteristics and properties of soluble recombinant proteins derived from Env-W. In particular.

The schematic structure of the various proteins produced from the vectors phCMV-Env-W, phCMV-EnvGp60 and phCMV-EnvSU is illustrated in FIG. 1a.

Production of the Soluble Envelope

The expression plasmid phCMV-EnvGp60 or phCMV-EnvSU is transfected into the HEK293T cells by precipitation with calcium phosphate. The supernatant containing the GP60 or SU envelope is collected after 48 hours of production in a serum-free medium and filtered on 0.45 μm membranes in order to remove the cellular debris. 20 μl of supernatant are directly analyzed on a polyacrylamide gel and by Western blotting with an anti-histidine monoclonal antibody (QIAGEN, RGS H6). The GP60 and SU proteins are correctly expressed in soluble form.

Binding Test and Analysis by Flow Cytometry

The stable lines XChASCT2 and XChASCT1 constitutively expressing the hASCT2 (XChASCT2) or hASCT1 (XChASCT1) receptors were established after transfection of XC cells (rat sarcoma) with vectors expressing either human receptor hASCT followed by selection of a clone as described above (Frendo et al., Mol. Cell Biol., Vol 23(10): 3566-3574, 2003). The following human cells are described in Blond J Virol, Vol 74(7): 3321-3329, 2000. The TE671 cells express hASCT2. The TE671RD cells constitutively express the RD114 envelope (cat endogenous retrovirus) belonging to the same interference group and therefore recognizing the hASCT2 receptor. TE671galv cells constitutively express the GALV (gibbon ape leukemia virus) envelope belonging to another interference group and recognizing the PiT1 receptor.

The cells were washed in PBS and harvested by detaching with 0.02% versene in PBS. A total of $10^6$ cells were incubated with 1 ml of filtered supernatant containing the soluble envelope (Gp60 or SU) for 1 hour at 37° C. The cells were washed with PBA (PBS and 0.5% sodium azide) containing 2% fetal calf serum and were labeled for 1 hour at 4° C. with an anti-histidine monoclonal antibody (RGSH6, QIAGEN). The cells were washed once with PBA and incubated with a secondary antibody coupled to fluorescein isocyanate for 1 hour at 4° C. The cells were washed twice with PBA and analyzed by flow cytometry.

Using the target cells XChASCT2, the inventors demonstrated that the recombinant protein Gp60 corresponding to a soluble form of the envelope has a phenotypical characteristic identical to that of the wild-type envelope, namely that it is capable of binding to XC cells expressing the hASCT2 receptor.

Figure 1B:
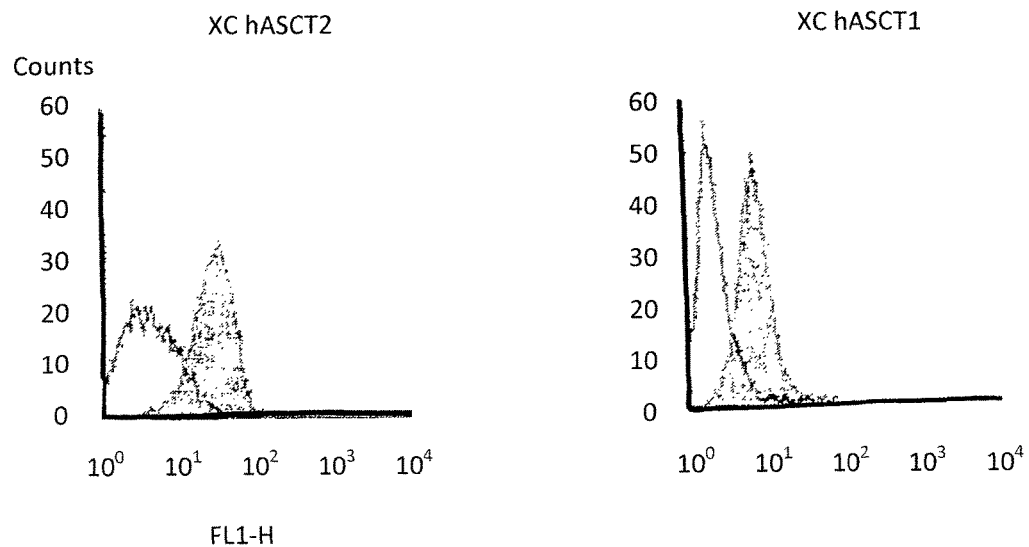
Figure 1C:
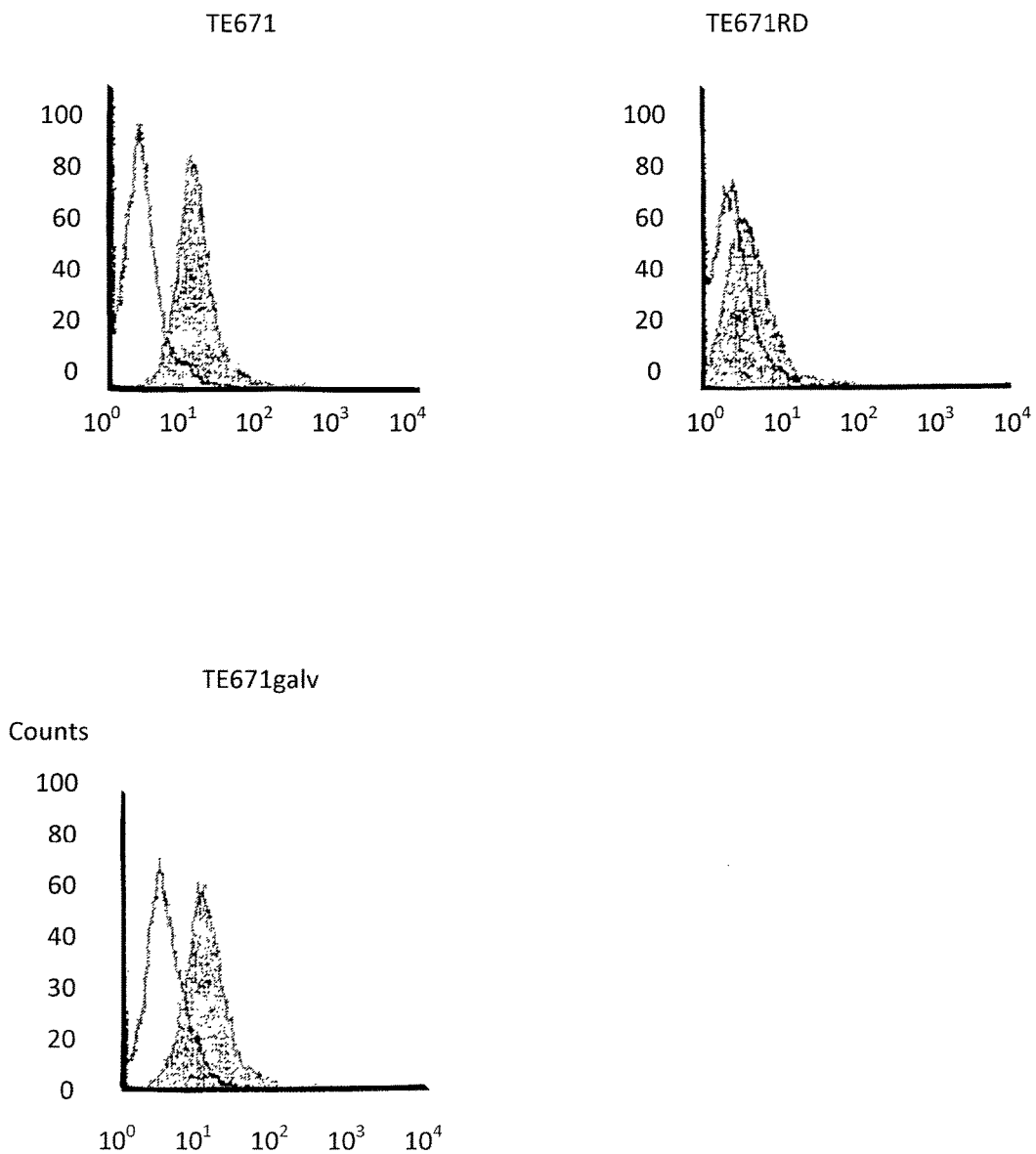

Using the target cells XChASCT2, XChASCT1, TE671, TE671RD, TE671 galv, the inventors demonstrated that the recombinant protein corresponding to the SU subunit of the envelope exhibits phenotypical characteristics identical to those of the wild-type envelope. First of all, the SU subunit is capable of binding to two receptors hASCT1 and hASCT2 (FIG. 1b). Furthermore, this protein was tested in relation to human cells TE671 and derived cells TE671RD and TE671galv. The soluble SU protein bound to the TE6781 cells expressing the hASCT2 receptor and the TE671galv cells blocked for the PiT1 receptor, but did not bind to the TE671RD cells blocked for the hASCT2 receptor (FIG. 1c). The SU recombinant protein and the envelope of the RD114 retrovirus specifically interfered.

Figure 2A:
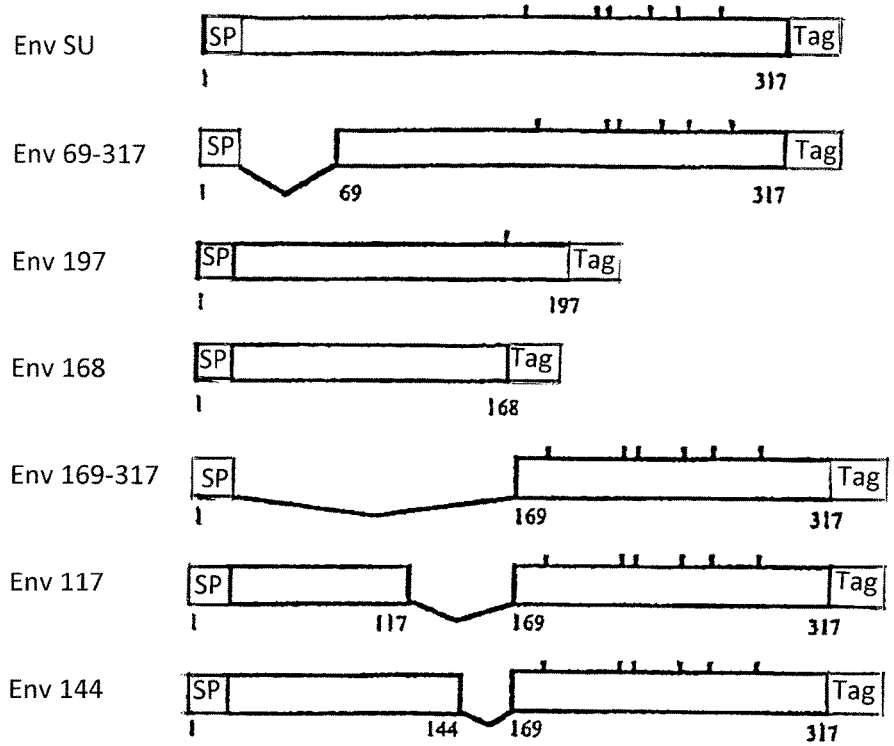
FIGS. 2a and 2b illustrate the definition of the minimum binding domain of the ERV-W envelope to the hASCT2 receptor (RBD for receptor binding domain). In particular, FIG. 2a describes all the deletion mutants designed from EnvSU.
Figure 2B:
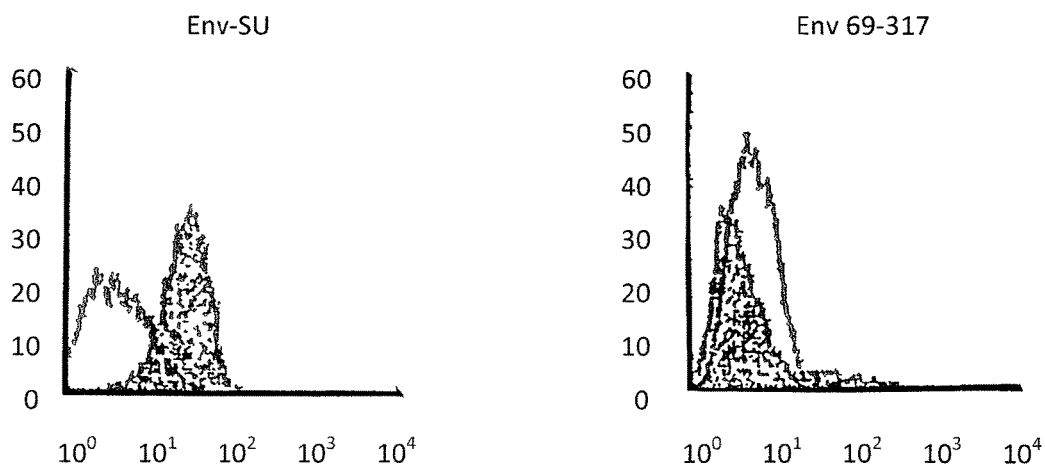
Figure 2B:
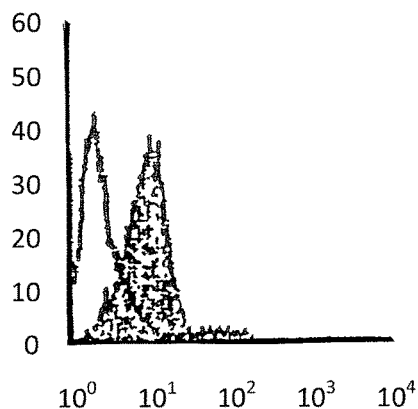
Figure 2B:
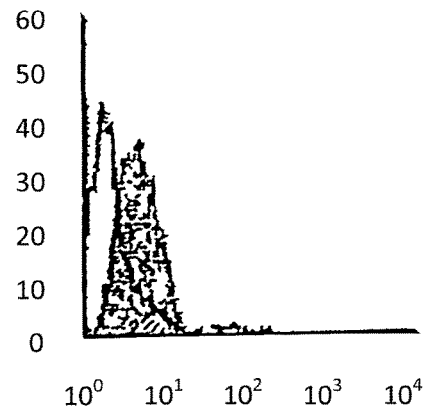
Figure 2B:
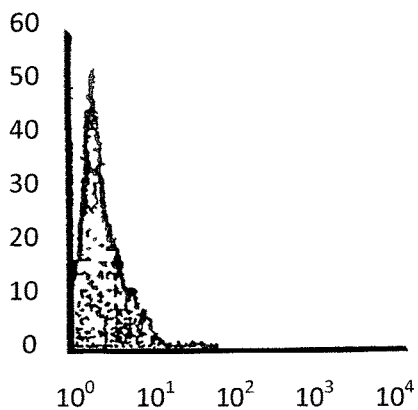
Figure 2B:
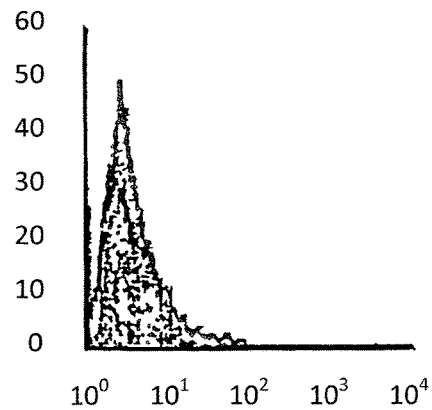
Figure 2B:
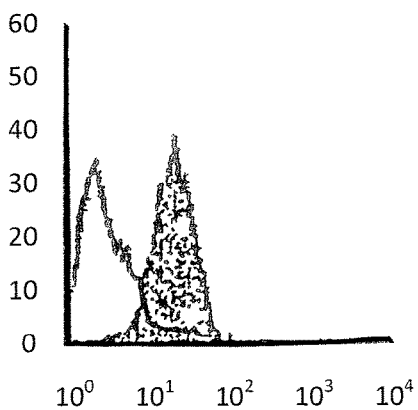
Figures 3A, 3B:
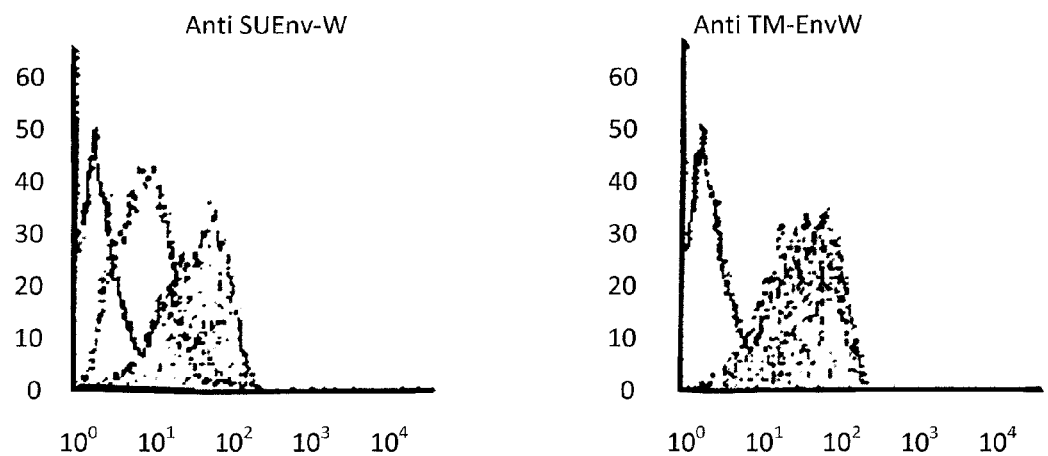
FIG. 3a illustrates the definition of an immunogenic peptide (SEQ ID NO: 74) inside the domain according to the invention (RBD) corresponding to region 21-144 of the precursor of the HERV-W envelope protein.
FIG. 3b shows the inhibition of the binding of the RBD to its receptor with the aid of an antibody produced from the immunogenic peptide (antiSU-EnvW) and the absence of inhibition of RBD-receptor binding in the presence of a nonspecific antibody (antiTM-EnvW).
Figure 4:
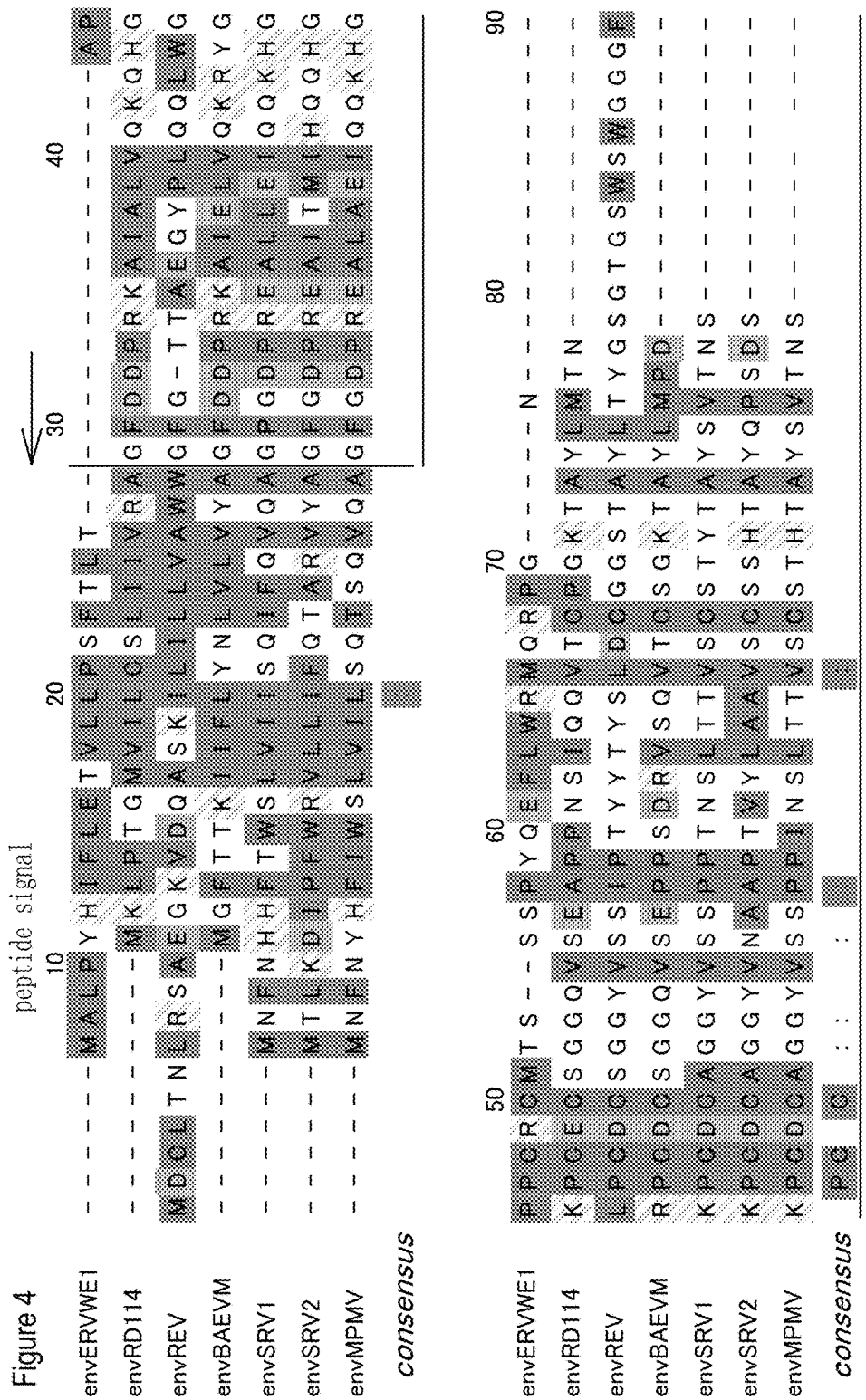
FIG. 4 represents the alignment of the retroviral envelope sequences belonging to the same interference group and shows the boundaries of the signal peptide, of the SU (surface unit) subunit and of the TM (Trans membrane) subunit and the receptor binding site. The sequences are SEQ ID NO: 75, SEQ ID NO: 76, SEQ ID NO: 77, SEQ ID NO: 78, SEQ ID NO: 79, SEQ ID NO: 80, and SEQ ID NO: 81, which are the envelope sequences, respectively, from HERV-W (Human Endogenous Retroviral Family W), RD114 (Cat Endogenous retrovirus), REV (Avian Reticuloendotheliosis Virus), BAEV (Baboon endogenous virus (strain M7)), SRV1 (Simian retrovirus SRV-1), SRV2 (Simian retrovirus SRV-2) and MPMV (Simian Mason-Pfizer virus).
Figure 4:
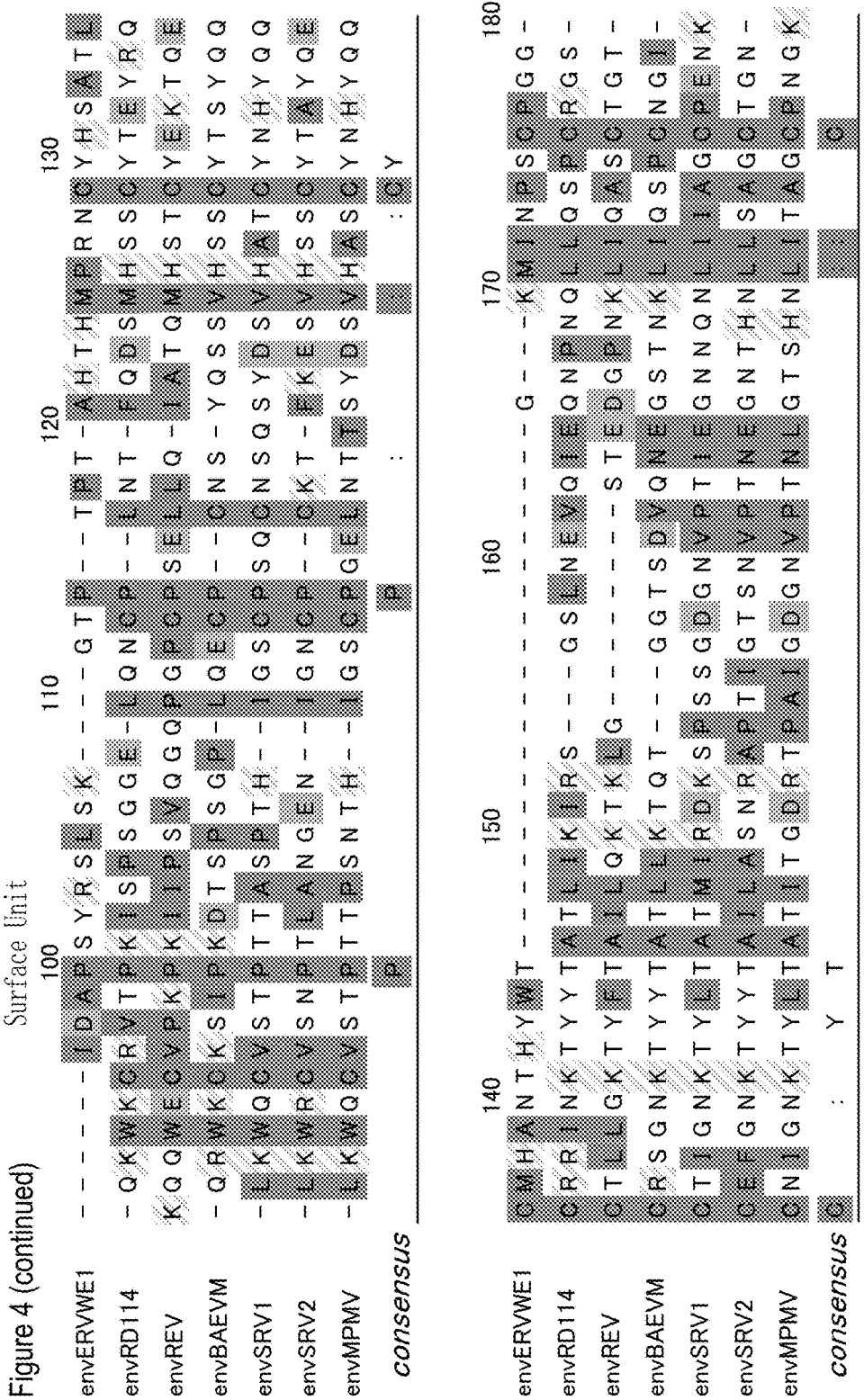
Figure 4:
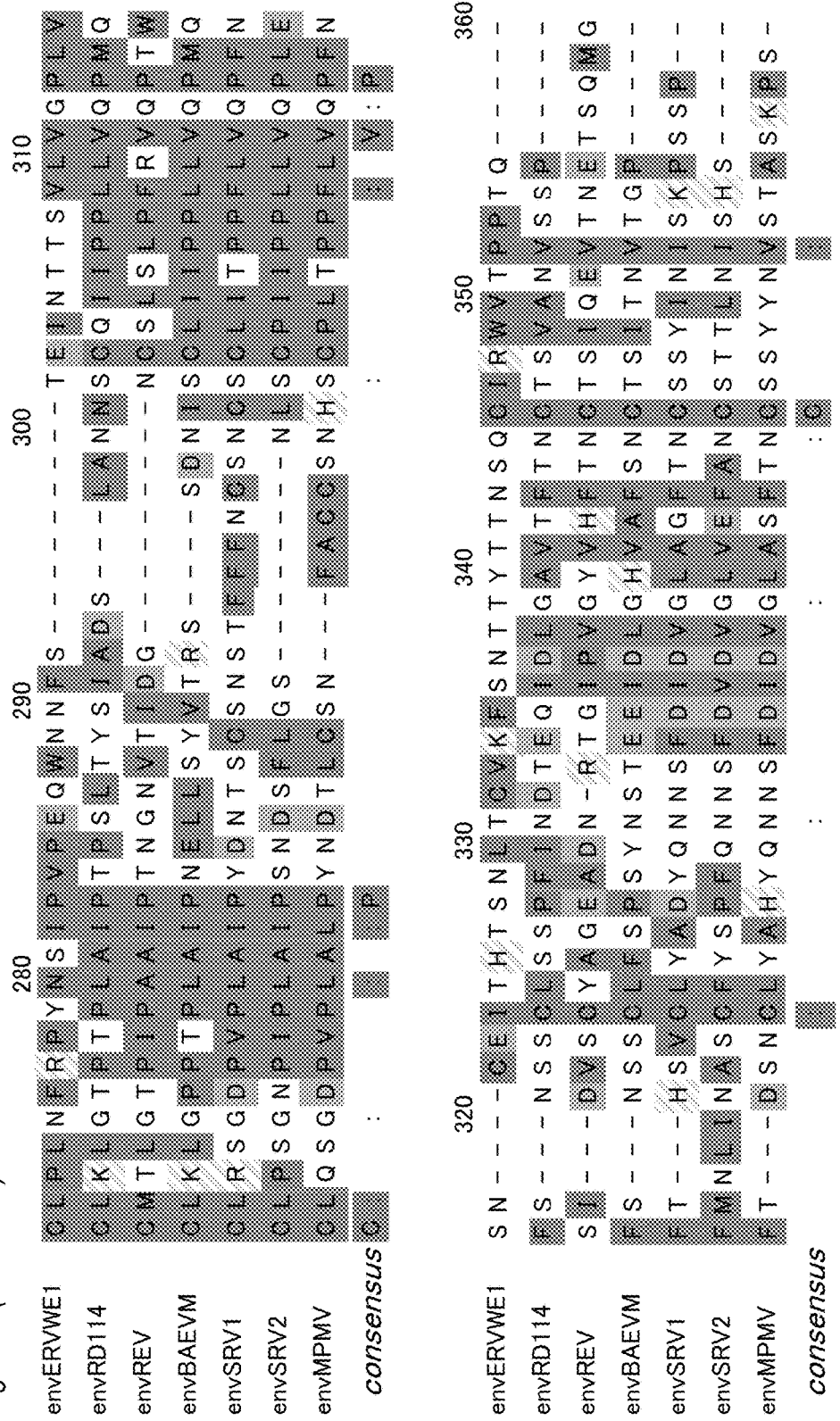
Figure 4:
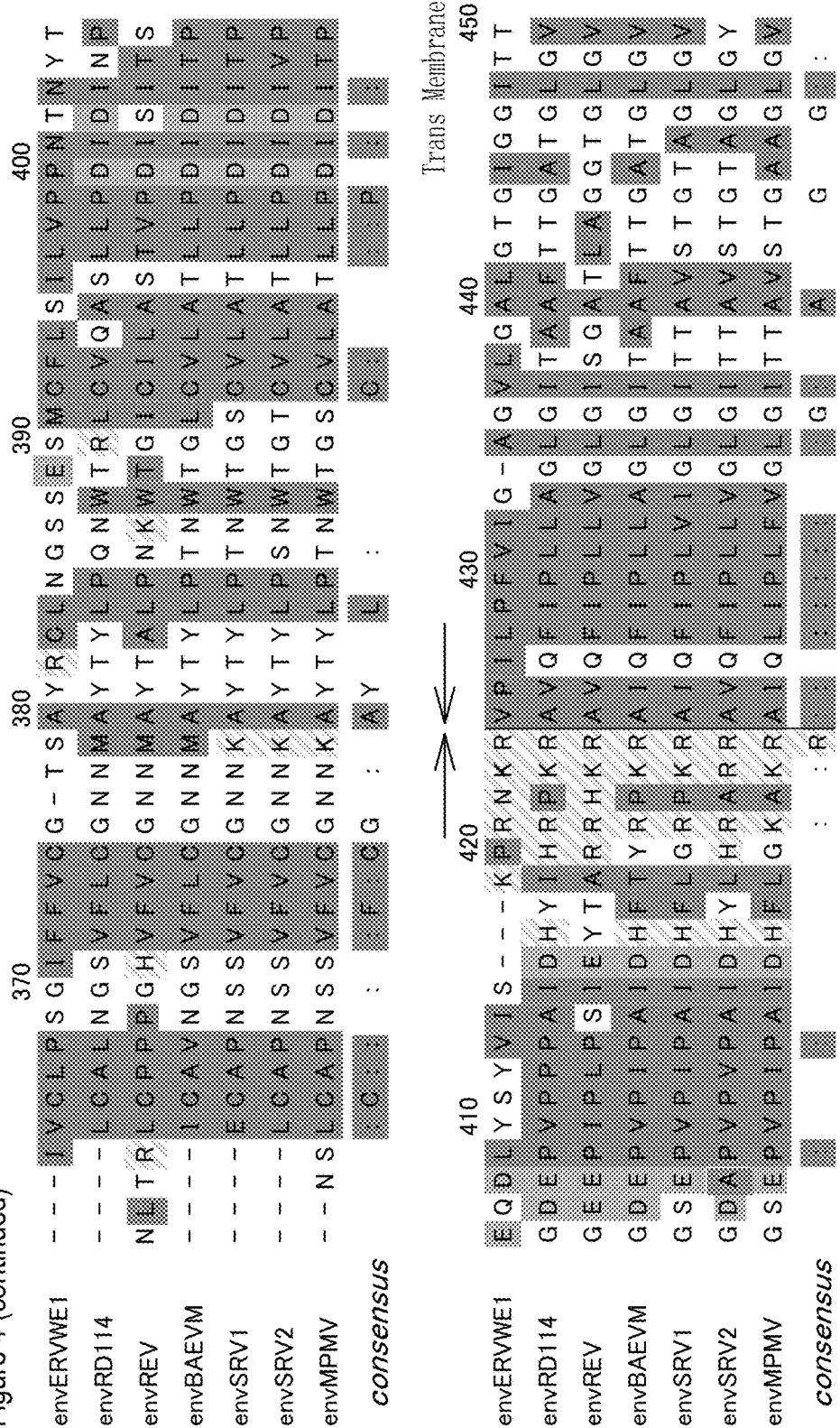
Figure 4:
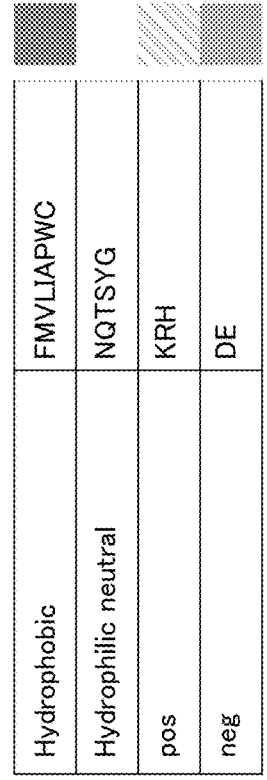
Figure 4:
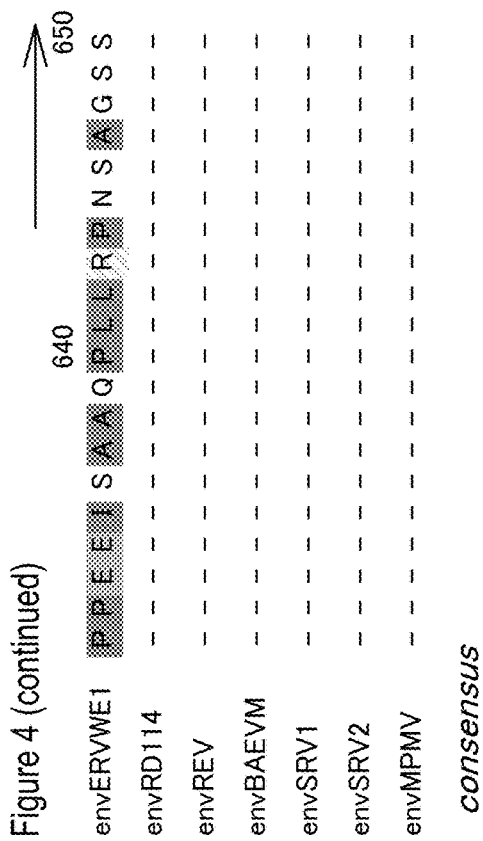

Example 2: Identification of the Domains for Interaction of the SU Part of the W Envelope with its hASCT2 Receptor In order to identify the boundaries of the region of the envelope binding to the hASCT2 receptor, the inventors constructed a set of deletion mutants from the N- and C-terminal ends. The domains of the SU subunit were obtained by PCR and subcloned into the expression vector pHCMV-EnvSU and sequenced. The expression plasmids phCMV-EnvSU, Env69-317, Env197, Env168, Env169-317, Env117 and Env144 (FIG. 2a) were transfected into the HEK293T cells by precipitation with calcium phosphate. The conditions for production and analysis of the proteins are identical to those detailed in example 1.

EnvSU, Env69-317 and Env197 proteins were correctly expressed in soluble form. Using the XC cells constitutively expressing hASCT2, the inventors demonstrated that the Env197 protein was capable of binding to the receptor expressed at the surface of the cells like the SU subunit (1-317). Thus, the first 176 residues of the mature SU subunit (and therefore lacking its signal peptide) were sufficient for binding to the surface of the cells expressing the hASCT2 receptor. The deletion of the 21-68 region resulted in a loss of binding to the receptor also indicating its involvement in the receptor binding domain (RBD). On the other hand, the truncated Env168 protein showed a lower capacity for binding to the hASCT2 receptor.

In order to obtain the equivalent quantities in the supernatants between the various truncated proteins, the inventors fused two smaller domains of the N-terminal region of SU (Env117 and Env144) to the C-terminal region of the SU subunit (Env169-317), the latter domain not binding to hASCT2. The level of expression of the Env117 and Env144 proteins was similar and the proteins were expressed in soluble form. The binding test showed that only the Env144 protein was capable of binding to the cells expressing the hASCT2 receptor. The absence of binding of the Env117 protein to the surface of the cells indicated the loss of at least one determinant of binding inside the 117-144 region.

Consequently, the boundaries of the domains for interaction of the W envelope with its receptor are defined by amino acids 21 to 144.

It should be noted that, in general, proteins (including the envelope proteins) intended for secretion or for membrane expression are synthesized in the granular endoplasmic reticulum (ER). The translocation of the neosynthesized proteins in the ER is conditioned by an N-terminal signal peptide (Walter and Lingappa 1986). The hydrophobic region of the signal peptide initiates penetration into the membrane of the reticulum, bringing behind it the remainder of the neosynthesized peptide. Since the translocation starts at the same time as the synthesis, it is the peptide being translated which crosses the ER membrane. While the protein passes into the lumene of the ER, the signal sequence is cleaved by a specific cellular enzyme, signal peptidase (Walter P, Johnson A E: Signal sequence recognition and protein targeting to the endoplasmic reticulum membrane. Annu. Rev. Cell Biol. 1994, 10: 87-119). The translocation of Env into the ER is stopped by the (hydrophobic) transmembrane domain of the glycoprotein which becomes anchored at the phospholipid membranes. In the ER lumene, the regions (SU and part of TM) intended to become extracytoplasmic are folded (the disulfide bridges formed), glycosylated and oligomerized. After oligomerization, the proteins undergoing maturation are transported into the Golgi apparatus where they undergo new glycan maturation processes and cleavage by furin-type endoproteases recognizing a motif R/KXXR leading to two SU and TM subunits.

The mature protein is targeted to the plasma membrane by virtue of a motif present on the intracytoplasmic tail containing a tyrosine (aliphatic/aromatic(Y-X-X)).

Example 3: Test of In Vitro Inhibition of the Binding of the Envelope to its Receptor (Definition of a Peptide and Generation of a Rabbit Antibody)

A peptide (112-129, TGMSDGGGVQDQAREKHV+C, 19 amino acids) (SEQ ID NO: 85) was defined from the region defined in example 2 and from a determination of the potentially antigenic regions of the SU subunit. A cysteine was added at the C-terminal position for the KLH (keyhole limpet hemocyanin, cf. Frendo et al., Mol. Cell Biol. Vol 23(10): 3566-3574, 2003) coupling. This peptide was used to immunize a rabbit and then to affinity purify the polyclonal antibody directed against the region 112-119 contained in the serum of this rabbit.

The Env144 protein is preincubated at 37° C. for one hour with either the anti-SU polyclonal antibody or with an anti-TM polyclonal antibody. The formation of the Env144 protein-anti-SU antibody complex drastically reduced the binding of the envelope to the cells expressing the hASCT2 receptor. By contrast, the use of an antibody not directed against the RBD did not adversely affect its binding to the hASCT2 receptor.

Example 4: Production of Monoclonal Antibodies Directed Against the HERV-W Envelope Protein Immunization of Mice with DNA Three female six-week-old BALB/c mice (IFFA-Credo) were immunized by direct injection of naked plasmid DNA (phCMV-env-W) containing the gene for the HERV-W envelope. The injections were performed by the intradermal route with the aid of a gene gun. Five injections of 2 μg of DNA were first performed for each mouse followed by a booster with two injections of 4 μg of DNA. The sera were collected and the antibody titer for each serum was determined. Since the antibody titer was too low, a cellular lysate was prepared.

Preparation of the Cellular Lysate

The rhabdomyosarcoma cells TelCeB6 (ATCC CRL8805) were transfected with the plasmid phCMV-env-W. After about hours and the presence of syncytia, a cellular extract was prepared in PBS buffer containing 0.5% TRITON. The protein extracts were assayed by Bradford. The env-W antigen concentration corresponded to 9.5 μg/μl of total proteins.

Immunization of Mice with an Extract of Cellular Lysate

The same mice first of all received an injection of 10 μg of cellular lysate by the intraperitoneal route followed by a booster injection of 2×100 μg of cellular lysate by the intraperitoneal route. Three days before the fusion with myeloma cells, another injection was performed, by the intravenous route, with 22 μg of soluble envelope protein Gp60 obtained from the plasmid phCMV-Env-Gp60 as described in example 1, purified beforehand, before injection, on to an Ni-NTA resin (QIAGEN) according to the following conditions: binding in phosphate buffer pH 8, washes in phosphate buffer pH 8 and in ammonium acetate pH 6, elution in ammonium acetate buffer pH 3.5 and concentration with speed vac. 47 μg of the eukaryotic Gp60 protein thus obtained were reserved for the injection by the intravenous route described above. After fusion, the hybridoma supernatants were tested by immunofluorescence on the transfected and bound cells (TeLCeb6), the antibodies were screened by a functional ELISA test using the Env-W protein at a concentration of 9.2 μg/μl of total proteins and an Env AS protein as negative control at a concentration of 13.3 μg/μl of total proteins and the most effective antibodies were selected.

The monoclonal antibodies 2H1H8, 12C7A3 and 1F11B10 were thus obtained. The monoclonal antibodies 2H1H8 and 12C7A3 are directed against the nonglycosylated N-terminal part of the SU region of the Env-HERV-W proteins. They are directed against the RDB as shown by a Western blot assay with the aid of Env 144. The monoclonal antibody 1F11B10 is directed against the glycosylated C-terminal part of the SU region of the Env-HERV-W protein as shown by a Western blot assay with the aid of Env 169-317. It does not recognize Env 144.

Example 5: Test of In Vitro Inhibition of the Binding of the Envelope to its Receptor and Inhibition of the Formation of Syncytia with the Aid of Monoclonal Antibodies by a Cell to Cell Fusion Test (Coculture)

The plasmid for expressing the envelope glycoprotein is transfected into the cells TELCeB6 by precipitation with calcium phosphate at two quantities 100 and 500 ng (Cosset et al., Journal of Virology, 69 (10): 6314-6322 (1995)). The cells expressing the envelope are detached from the support 20 hours after transfection and are preincubated at 37° C. for one hour, respectively, with the anti-HIV 23A5 monoclonal antibody, the anti-TM Env-HERV-W 6A2B2 monoclonal antibody (previously obtained), the anti-SU Env-HERV-W 2H1H8 12C7A3 and 1F11B10 monoclonal antibodies (dilution 1/50th). Next, they are reinoculated at equal concentration ($0.4\times10^5$ cells/well) into 12-well plates. Epithelioid-carcinoma-indicating human cells (Hela, ATCC CCL-2) are then added to the transfected cells in an amount of $2\times10^5$ cells per well and the co-culture is continued for 24 h. An XGal (5-bromo-4-chloro-3-indolyl-β-D-galactopyranoside) staining may then be performed in order to stain the nucleus of the cells TELCeB6 (Cosset et al., Journal of Virology, 69 (10): 6314-6322 (1995)). It is followed by staining with May-Grünwald and Giemsa solutions (MERCK) performed according to the suppliers' recommendations. The fusion observed corresponds to a fusion “from within”, that is to say a cell to cell fusion, starting with a cell expressing the envelope, in contrast to a fusion “from without” which corresponds to a formation of syncytia following a virion-cell(s) fusion.

The results presented in table 1 below express the number of fused cells counted.

TABLE 1

| Antibody | 23A5 | 6A2B2 | 2H1H8 | 1F11B10 | 12C7A3 |
|---|---|---|---|---|---|
| 100 ng | 261 | 231 | 130 | 223 | ND |
| 500 ng | 217 | 273 | 73 | 210 | 11 |

ND: not determined

The results presented above show that the formation of the Env protein-anti-SU 2H1H8 and 12C7A3 antibody complex dramatically reduces the binding of the envelope to cells expressing the hASCT2 receptor and cell fusion. By contrast, the use of an antibody not directed against rdb (6A2B2 or 1F11B10) does not adversely affect the binding of the envelope and the fusion of the cells significantly, as may be observed by comparing to the results obtained with the anti-HIV 23A5 control antibody.

Example 6: Study of the In Vivo Interaction Between the Envelope Protein and the hASCT2 Receptor and the In Vivo Formation of Syncytia To verify the results obtained in vitro, an animal model was designed. Rhabdomyosarcoma cells TelCeB6 (ATCC CRL8805), in culture in DMEM medium (GIBCO INVITROGEN 41966-029) supplemented with South American serum, were respectively transfected, with the aid of the LIPOFECTAMINE PLUS™ kit (GIBCO INVITROGEN), with the DNA corresponding to the HERV-W env gene cloned in the sense orientation at the concentration of 2 µg/µl (DNA 409), with the DNA corresponding to the HERV-W env gene cloned in the anti-sense orientation at the concentration of 1.5 µg/µl (DNA 410) and with the DNA corresponding to a mutated HERV-W env gene at the concentration of 1.3 µg/µl (DNA LQMV) according to the protocol detailed below. The cells transfected with the DNA 409 are capable of expressing the fusogenic W envelope protein, the cells transfected with the DNA 410 are not capable of expressing the envelope protein and the cells transfected with the DNA LQMV are capable of expressing a nonfusogenic mutated W envelope protein.

1). Protocol:
1st Day: Culture of the TelCeB6 Cells:
inoculation of the dishes 100 mm in diameter→50-70% confluence;
incubation in supplemented DMEM medium (6 ml per dish) for 24 hours at 37° C. under 5% $CO_2$.
2nd Day: Transfection with the LIPOFECTAMINE PLUS™ Kit:
1 Precomplexing of the DNA
mixing of 750 µl of medium not supplemented with the abovementioned DNAs in a 15 ml falcon tube (reference 2096), that is 2 µl of 409 or 3 µl of 410 or 3 µl LQMV;
stirring under vortex of PLUS reagent and adding 20 µl thereof to the DNA solution;
stirring under vortex immediately 10 seconds at 1400 rpm;
incubation 15 minutes at room temperature.
2 Preparation of the Cells
replacement with 5 ml of nonsupplemented medium.
3 Dilution of the LIPOFECTAMINE
In a tube for a dish, mix 30 µl of LIPOFECTAMINE Reagent with 750 µl of nonsupplemented medium.

4 Complexing of the DNA
Mixing of 780 µl of dilute LIPOFECTAMINE and 772 µl of solution of precomplexed DNA (total: 1552 µl);
stirring under vortex immediately 10 sec at 1400 rpm, incubation 15 minutes at room temperature.

5 Transfection and Production of Recipient Animals Transplanted with the Target Cells, Treated or not Treated by Injection of Anti-Env Antibody
Deposition of 1552 µl in a dish;
incubation 2-3 hours at 37° C. under 5% $CO_2$;
replacement of the transfection medium with 6 ml of supplemented medium;
incubation 1 hour at 37° C. under 5% $CO_2$;
injection by the intraperitoneal route (IP) to SCID mice (in a volume of 1 ml), ⅕th of each dish at 70% confluence, with or without additional injection of anti-Env protein antibody (monoclonal antibody 2H1H8, polyclonal antibody 69 (anti-SU) and 71 (anti-TM) at ¹⁄₁₀₀).
Production of animals tolerating the transplant and allowing dissemination of the transplanted cells in the body, in parallel with the establishment of pseudo-ascites in the peritoneal cavity.
3rd Day:
Collection of the cells from each animal by peritoneal lavage: injection of 2 ml of air followed by 2 ml of physiological saline and then massaging and recovering the 2 ml of peritoneal fluid (protocol developed for the recovery, in transplanted animals, of the cells implanted in the peritoneal cavity);
observation under an "inverted phase" microscope with counting of the syncytia and/or after staining on a slide;
immediate reading performed after spreading on slides with a gridded chamber in the presence of Trypan blue (exclusion of the dead cells). The number of cells which have fused to each other was counted per field with a "wide angle" lens (40) which makes it possible to establish the count on more than about one hundred cells so as to have a series of statistically representative counts.
A cellular aliquot of each sample is fixed in the presence of methanol/acetone (v/v) and then stored at −20° C. until a crystal violet staining is obtained (1%). Photographs were taken of the stained slides.
2) Mice:
Groups of 2 mice are inoculated with:
the cells transfected with the three types of plasmid (DNAs 409, 410 and LQMV) with no antibody (3×2=6 mice) the cells transfected with the three types of plasmid (DNAs 409, 410 and LQMV) with the monoclonal antibody 2H1H8 (3×2=6 mice).
3) Results:
The number of fused cells determined by direct reading on a gridded counting chamber per 100 cells is indicated in Table 2 below:

TABLE 2

| ECP (Tryptan blue) reading: direct reading of the syncytia | | | |
|---|---|---|---|
| Lines | S1* count | S2* count | Mean |
| 409 control | 19 | 22 | 20.5 |
| 409 + 2H1H8 | 3 | 4 | 3.5 |
| 410 control | 8 | 11 | 9.5 |
| 410 + 2H1H8 | 2 | 3 | 2.5 |
| LQMV control | 8 | 5 | 6.5 |
| LQMV + 2H1H8 | 1 | 1 | 1 |

S1* and S2* = mouse 1 and mouse 2

Each number represents the number of fused and visualized cells per field studied. As some cells may be superposed in the optical path, the count for the cells appearing fused in the controls is greater than zero. The reality of the syncytia and the discrimination with stacks of cells were then verified by staining the cells on a slide, with visualization of multiple cell nuclei contained in a space delimited by the continuation of a single and sole cell membrane. Moreover, photos showing cells in the course of fusion made it possible to objectify the reality of the fusion upon analysis by phase contrast microscopy and the total absence of an equivalent phenomenon in the controls.

To statistically objectify the primary analysis represented by the numbers indicated in Table 2, a Chi-test was performed in order to compare the data in Table 2.

The results of the statistical analysis taking into account the "background noise" of the primary reading, without secondary analysis after staining on a slide or a search for typical cells in the course of fusion which are never seen in the controls, are the following:

i) Statistical validation of the specificity of the pathogenic effect in vivo:

Env expressed (409): 20.5 positives counted on average out of 100 cells, anti-sense Env (410): 9.5 positives counted on average out of 100 cells, mutated Env (LQMV): 6.5 positives counted on average out of 100 cells, mean of the controls (410 and LQMV): 9.5+6.5/2=8%.

Env versus control 410: Chi-2=5.89 ($p<0.02$)

Env versus control LQMV: Chi-2=9.83 ($p<0.002$)

Env versus the two controls (410 and LQMV): Chi-2=7.69 ($p<0.01$)

Control 410 versus control LQMV: Chi-2=0.61 (difference not significant).

The controls are therefore statistically equivalent and there is no "real" difference linked to the type of control.

The results obtained from this stage of analysis (not excluding the background noise linked to the artefactual images and by comparing the two types of control with each other (which prove to be equivalent)) was statistically very significant (overall $p<0.01$). Subsequent analysis, by staining, of the specificity of the effects therefore merely confirm the specificity of the effect obtained in vivo in the presence of the Env protein, thereby validating the animal model of the in vivo study of syncytia whose fusion was induced by HERV-W Env.

ii) Statistical validation of the therapeutic activity of the antibodies tested on the pathogenic effect in vivo:

Env expressed (409): 20.5 positives counted on average out of 100 cells,

Env expressed (409)+monoclonal antibody 2H1H8: 3.5 positives counted on average out of 100 cells.

Env alone versus single injection of the antibody 2H1H8: Chi-2=15.38 ($p<0.001$)

The results obtained show a statistically significant effect for the monoclonal antibody (probability of result due to chance (p) less than 0.001). Subsequent analyses, by staining, of the specificity of the effects merely confirm the specificity of the effect obtained in vivo in the presence of the Env protein and of antibody, thereby validating the therapeutic effect on the animal model.

Example 7: Study In Vivo of the Binding of the HERV-W Env Protein to Cells Possessing or not Possessing Type 1 or 2 hASCT Receptors and of the Inhibition of this Binding by Injection of Antibodies Directed Against HERV-W Env 1) Materials Soluble protein: supernatant filtered on 0.45 µm containing the soluble protein (293T cells transfected with the plasmid 460 (envelope-spacer-His6).

Expression verified by Western blotting with an anti-RGS-His antibody.

Antibody: monoclonal antibody 2H1H8 (IgG, 5.50 mg/ml).

Cells: XChASCT2, cellular clone XC (ATCC CCL-165, rat cells) expressing the hASCT2 receptor.

DMEM medium (GIBCO INVITROGEN 41966-029) with South American serum.

Preincubation, incubation, labeling in a 1.5 ml EPPENDORF tube.

2) Protocol

1 IP (intraperitoneal) inoculation of the XChASCT1, XChASCT2 cells and control cells XChASCT—into SCID mice Injection into mice of ⅕th of the flask at 70% confluence in a volume of 2 ml.

2 Preincubation

Incubation of the soluble protein supernatant (filtered supernatant of the 293T line) with the monoclonal antibody 2H1H8 (990 µl of supernatant with 10 µl of antibody (¹/₁₀₀th dilution)) for 1 hour at 37° C. in the cell incubator with occasional stirring (every 15 minutes).

3 Inoculation

IP (intraperitoneal) inoculation of the proteins alone or with the antibody into mice transplanted with the cells ($1 \times 10^6$ cells per point, that is ⅕th of a confluent dish 100 mm in diameter).

After injection of the antibody (200 microliters), maintained as IP, for 6 hours, with an occasional peritoneal massage (every 30-60 minutes).

4 Recovery of the Cells by Peritoneal Lavage of the Transplanted Mice

Centrifugation 3000 revolutions for 5 minutes at +4° C.

Recovery of the cellular pellet and dilution in the labeling media (maintained at +4° C. until fixing).

5 Labeling

Primary antibody:

The pellet is taken up in 100 µl of anti-RGS His antibody (100th dilution—QIAGEN) in a PBA buffer (PBS with 2% fetal calf serum and 0.1% sodium azide), maintained at +4° C.

1 hour in ice with occasional stirring (every 15 minutes).

Washing in PBA buffer (1 ml per tube), maintained at +4° C.

Secondary antibody:

Centrifugation 3000 revolutions for 5 minutes at +4° C. The pellet is taken up in 100 µl of anti-mouse antibody-FITC (¹/₂₀th dilution—DAKO, reference F0479 in a PBA buffer) maintained at +4° C.

1 hour in ice with occasional stirring (every 15 minutes).

2 washes in PBA buffer (1 ml per tube), maintained at +4° C.

Pellet taken up in 500 µl of PBA, maintained at +4° C., and analyzed by FACS.

Alternatively, analysis by IF after fixing on a slide in acetone/methanol (50%/50%) at −20° C. and counter-staining with Evans blue.

3) Mice:

Groups of 2 mice are inoculated with:

each type of cell (expressing the 2 types of receptor hASCT1 and hASCT2 and one not expressing the receptor hASCT—as a control) with no antibody (3×2=6 mice)

the three types of cell with the Env protein and the monoclonal antibody 2H1H8 (3×2=6 mice).

4) Results

The results by immunofluorescence (IF) reading with a microscope are presented in Table 3 below:

TABLE 3

IF reading: number of fluorescent cells/total
number of cells (NF/NT) in the same field

| Lines | NF/NT | Mean |
| --- | --- | --- |
| XC control | 1/18, 0/10 | 1/28 |
| XC + 2H1H8 | 0/20 | 0/20 |
| XChASCT1 control | 12/40, 3/12, 9/25 | 24/77 |
| XChASCT1 + 2H1H8 | 1/25, 0/18, 1/30 | 2/73 |
| XChASCT2 control | 8/22, 15/35 | 23/57 |
| XChASCT1 + 2H1H8 | 1/45 | 1/45 |

Each number represents the number of cells visualized as fluorescent per field studied. As some cells may have bound fluorescence in a non-specific manner, the count for the cells appearing fluorescent under the control conditions is therefore greater than zero in one of the two fields counted (mean of the two fields=½8, that is 0.036%, which is entirely reasonable for the background noise of such a reading technique). The reality of the cells that bound the Env protein to their hASCT1 or hASCT2 receptor was then verified by cytofluorometric analysis.

In order to statistically objectify the analysis presented in Table 3, a Chi-2 test was performed in order to compare the data obtained under the conditions according to which (i) the Env protein can bind to a receptor hASCT1 (control hASCT1) or hASCT2 (control hASCT2) present at the surface of the cells transplanted into SCID mice versus the grafted control cells which have no receptor (control X) to which the Env protein injected into the corresponding animals cannot bind and thus does not give membrane fluorescence in the presence of an anti-Env antibody and (ii) the Env protein can bind to a receptor hASCT1 (control hASCT1) or hASCT2 (control hASCT2) present at the surface of the cells transplanted into SCID mice versus the injection of a monoclonal antibody directed against Env-SU.

The results of the statistical analysis are presented below:

i) Statistical validation of the specificity of the pathogenic effect in vivo:

control hASCT1: 24 positives counted on average out of 77 cells, control hASCT2: 23 positives counted on average out of 57 cells, hASCT- cells: 1 positive counted on average out of 28 cells.

Env+grafts hASCT1 versus hASCT-: Chi-2=8.62 (p<0.01)

Env+grafts hASCT2 versus hASCT-: Chi-2=12.53 (p<0.001)

Env+grafts hASCT1 versus env+grafts hASCT2: Chi-2=1.21 (difference not significant).

The cells expressing the hASCT1 or hASCT2 receptors at their surface are therefore indeed statistically equivalent and there is no difference in the Env binding to the receptor linked to subtype 1 or 2, under the conditions of the experiment.

The results obtained with the animals transplanted with the cells expressing the membrane receptors hASCT1 or hASCT2 are statistically significant in the light of the results obtained with the control animals transplanted with the cells expressing none of these receptors at their surface.

These results confirm the specificity of the effect obtained in vivo in the presence of the Env protein in the animal models.

ii) Statistical validation of the therapeutic activity of the antibodies tested on the pathogenic effect in vivo:

Env+grafts control hASCT1: 24 positives counted on average out of 77 cells

Env+grafts hASCT1+monoclonal antibody 2H1H8: 2 positives counted on average out of 73 cells.

Env+grafts hASCT1 alone versus injection antibody 2H1H8: Chi-2=21.14 (p<0.001)

The results obtained show a statistically significant effect for the monoclonal antibody (probability of the result due to chance (p) less than 0.001).

Env+grafts hASCT2: 23 positives counted on average out of 57 cells

Env+grafts hASCT2+monoclonal antibody 2H1H8: 1 positive counted on average out of 45 cells.

Env+grafts hASCT2 alone versus injection antibody 2H1H8: Chi-2=20.31 (p<0.001).

The results obtained show a statistically significant effect for the monoclonal antibody (probability of the result due to chance (p) overall less than 0.01).

The validation of the animal models against the appropriate controls makes it possible to demonstrate that antibodies may have a therapeutic activity by significantly inhibiting the pathogenic effects of the HERV-W Env protein.

Example 8: Alignment of the Sequences of the Interference Group

The protein sequences of the envelopes of the retroviruses HERV-W (swiss-prot Q9UQF0), RD114 (swiss-prot Q98654), REV (swiss-prot P31796), BAEV (swiss-prot P10269), SRV1 (swiss-prot P04027), SRV2 (swiss-prot P51515) and MPMV (swiss-prot P07575) were aligned with the aid of the MACVECTOR software with the CLUSTALW procedure. The signal peptide, the SU (surface unit) subunit and the TM (Trans membrane) subunit are indicated. The receptor binding site is underlined.

The invention claimed is:

1. A method comprising:
chemically synthesizing a peptide; or
performing genetic engineering to produce the peptide,
wherein the peptide is no longer than the receptor binding domain of the HERV-W envelope protein and comprises:
an N-terminus motif including an amino acid sequence selected from the group consisting of SEQ ID NO: 1 to SEQ ID NO: 29;
a C-terminus motif including an amino acid sequence selected from the group consisting of SEQ ID NO: 30 to SEQ ID NO: 40; and
at least one motif between the N-terminus and the C-terminus including an amino acid sequence selected from the group consisting of SEQ ID NO: 41, SEQ ID NO: 42, and SEQ ID NO: 73.

2. The method of claim 1, wherein the Xaa of the Pro Cys Xaa Cys motif in SEQ ID NO: 1 to SEQ ID NO: 29 is aspartic acid, glutamic acid, or arginine.

3. The method of claim 1, wherein the amino acids at positions 3, 4, and 5 of SEQ ID NO: 30 to SEQ ID NO: 40 are glycine.

4. The method of claim 1, wherein the amino acid at position 6 of SEQ ID NO: 30 to SEQ ID NO: 40 is proline or valine.

5. The method of claim 1, wherein the amino acid at position 7 of SEQ ID NO: 30 to SEQ ID NO: 40 is glutamine, leucine, or threonine.

6. The method of claim 1, wherein the amino acid at position 9 of SEQ ID NO: 30 to SEQ ID NO: 40 is lysine, threonine, methionine, or glutamine.

7. The method of claim 1, wherein the amino acid at position 10 of SEQ ID NO: 30 to SEQ ID NO: 40 is alanine, lysine, isoleucine, threonine, or valine.

8. The method of claim 1, wherein the peptide comprises SEQ ID NO: 41 in which the amino acid at:
position 3 is asparagine, threonine, glutamic acid, or histidine;
position 4 is histidine, alanine, serine, lysine, or glutamic acid;
position 5 is tyrosine, threonine, or alanine;
position 6 is glutamine, arginine, or threonine; and
position 7 is leucine, glutamine, or glutamic acid.

9. The method of claim 1, wherein the peptide comprises SEQ ID NO: 42 in which the amino acid at:
position 2 is proline, threonine, arginine, or asparagine;
position 3 is glycine, glutamic acid, or asparagine;
position 4 is glycine, asparagine, isoleucine, threonine, or serine;
position 5 is lysine or not present;
position 6 is lysine, valine, isoleucine, or leucine;
position 7 is glycine or asparagine;
position 8 is glutamine, lysine, or valine;
position 9 is valine, proline, serine, or threonine; and
position 10 is valine or isoleucine.

10. The method of claim 1, wherein the peptide comprises SEQ ID NO: 73 in which the amino acid at:
position 2 is proline, threonine, arginine, or asparagine;
position 3 is glycine, glutamic acid, or asparagine;
position 4 is glycine, asparagine, isoleucine, threonine, or serine;
position 5 is lysine, valine, isoleucine, or leucine;
position 6 is glycine or asparagine;
position 7 is glutamine, lysine, or valine;
position 8 is valine, proline, serine, or threonine; and
position 9 is valine or isoleucine.

11. The method of claim 1, wherein the peptide has the amino acid sequence of SEQ ID NO: 74.

12. The method of claim 1, wherein the peptide is chemically synthesized.

13. The method of claim 1, wherein the peptide is produced by genetic engineering.

14. The method of claim 13, wherein the peptide is produced by a genetic engineering technique comprising:
culturing a microorganism or eukaryotic cells that include a nucleotide sequence encoding the peptide so as to express the peptide; and
recovering the peptide expressed by the microorganism or eukaryotic cells.

15. The method of claim 14, wherein the microorganism or eukaryotic cells include the nucleotide sequence and elements necessary for expressing the nucleotide sequence.

16. The method of claim 1, further comprising:
immunizing an animal with the peptide to produce an antibody-producing lymphocyte;
fusing the antibody-producing lymphocyte with an immortal cell to produce a hybridoma; and
multiplying the hybridoma to produce a monoclonal antibody.

17. The method of claim 1, wherein the peptide is no longer than SEQ ID NO: 74.

* * * * *